United States Patent
Byram et al.

(10) Patent No.: US 11,813,110 B2
(45) Date of Patent: Nov. 14, 2023

(54) ADVANCED ULTRASOUND IMAGING TECHNIQUES FOR KIDNEY STONE DETECTION AND CHARACTERIZATION

(71) Applicant: VANDERBILT UNIVERSITY, Nashville, TN (US)

(72) Inventors: Brett C. Byram, Nashville, TN (US); Ryan S. Hsi, Nashville, TN (US); Jaime E. Tierney, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 1081 days.

(21) Appl. No.: 16/432,731

(22) Filed: Jun. 5, 2019

(65) Prior Publication Data
US 2019/0365345 A1    Dec. 5, 2019

Related U.S. Application Data

(60) Provisional application No. 62/680,834, filed on Jun. 5, 2018.

(51) Int. Cl.
| | | |
|---|---|---|
| *A61B 8/08* | (2006.01) | |
| *G06T 11/00* | (2006.01) | |
| *G06T 7/00* | (2017.01) | |
| *G06T 7/60* | (2017.01) | |
| *G06T 7/11* | (2017.01) | |

(52) U.S. Cl.
CPC ............ *A61B 8/085* (2013.01); *A61B 8/5223* (2013.01); *G06T 7/0012* (2013.01); *G06T 7/11* (2017.01); *G06T 7/60* (2013.01); *G06T 11/003* (2013.01); *G06T 2207/10132* (2013.01); *G06T 2207/30084* (2013.01)

(58) Field of Classification Search
CPC ....... A61B 8/085; A61B 8/469; G06T 7/0012; G06T 7/11; G06T 2207/30084
See application file for complete search history.

(56) References Cited

U.S. PATENT DOCUMENTS

| | | | |
|---|---|---|---|
| 2011/0263967 A1* | 10/2011 | Bailey | A61B 17/2256 600/453 |
| 2015/0320383 A1* | 11/2015 | Dunmire | A61B 8/0875 600/443 |
| 2017/0209121 A1* | 7/2017 | Davis, Sr. | A61B 8/4494 |

OTHER PUBLICATIONS

Kruizinga, Pieter, et al. "Compressive 3D ultrasound imaging using a single sensor." Science advances 3.12 (2017): e1701423. (Year: 2017).*

(Continued)

*Primary Examiner* — John Denny Li
(74) *Attorney, Agent, or Firm* — NIXON PEABODY LLP

(57) ABSTRACT

The present disclosure is directed towards systems and methods for detecting and sizing mineralized tissue. An exemplary method, according to an embodiment of the present disclosure, can provide for imaging a region of interest containing the mineralized tissue with unfocused ultrasound beams via a primary imaging method. The method can then provide for computing a wavefront coherence at the imaged region of interest. The method can then provide for segmenting pixels of the imaged region of interest based on their intensities and intensities of surrounding pixels. The method can then provide for identifying a border and a shadow of the mineralized tissue based on the segmenting. Then, the method can provide for calculating a size of the mineralized tissue based on the border and the shadow.

14 Claims, 22 Drawing Sheets

(56) References Cited

OTHER PUBLICATIONS

Dunmire, Barbrina, et al. "Tools to improve the accuracy of kidney stone sizing with ultrasound." Journal of endourology 29.2 (2015): 147-152. (Year: 2015).*
Jensen, Jørgen Arendt, et al. "Synthetic aperture ultrasound imaging." Ultrasonics 44 (2006): e5-e15. (Year: 2006).*
Go, Dooyoung, et al. "Efficient transmit delay calculation in ultrasound coherent plane-wave compound imaging for curved array transducers." Applied Sciences 9.13 (2019): 2752. (Year: 2019).*
S. Schlunk et al., "Non-linear beamforming approaches for sizing and detecting large calcifications," 2017 IEEE International Ultrasonics Symposium (IUS), Washington, DC, USA, 2017, pp. 1-4, doi: 10.1109/ULTSYM.2017.8092597. (Year: 2017).*
Lediju MA, Trahey GE, Byram BC, Dahl JJ, "Short-lag Spatial Coherence of Backscattered Echoes: Imaging Characteristics", IEEE Trans Ultrason Ferroelectr Freq Control, 2011:58(7):1377-1388.

* cited by examiner

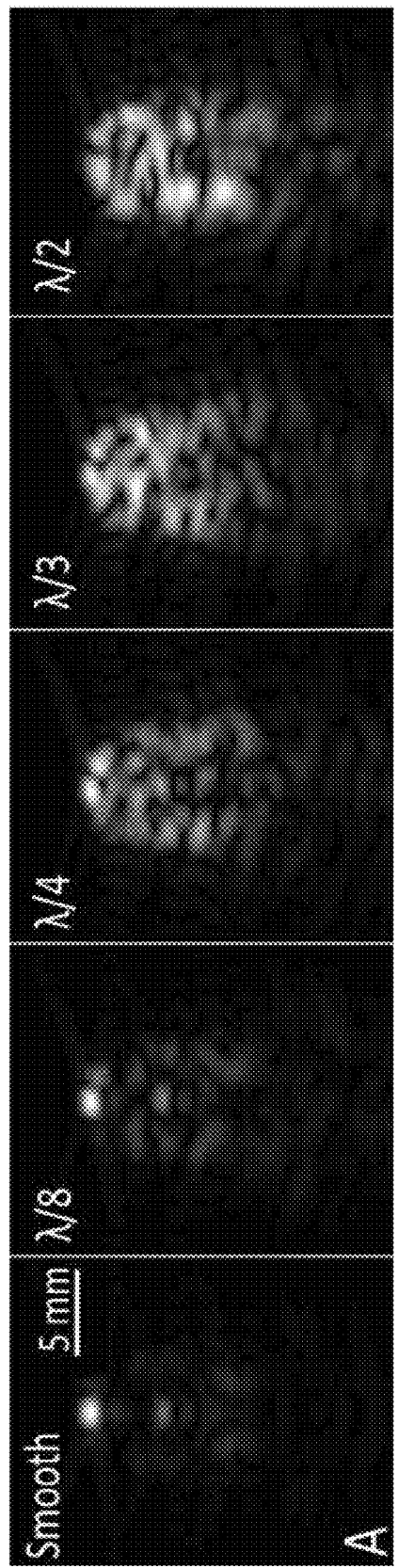
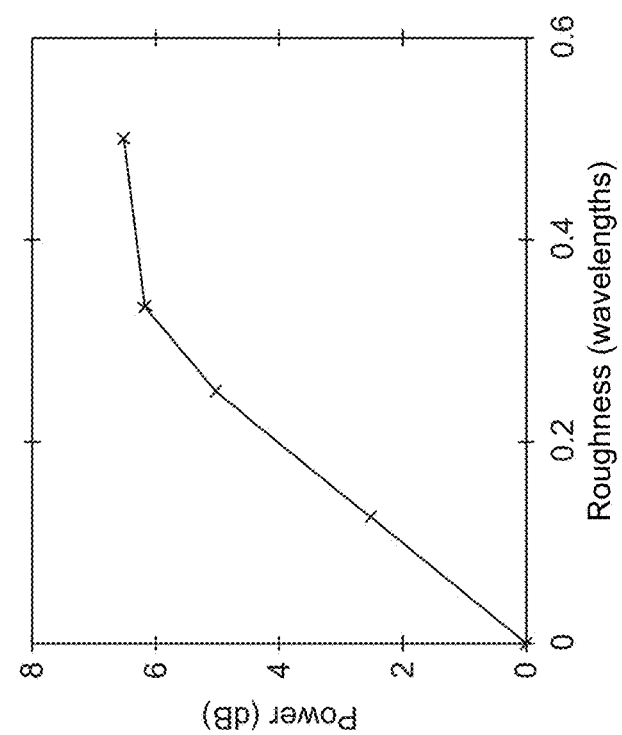
FIG. 21A
FIG. 21B

ADVANCED ULTRASOUND IMAGING TECHNIQUES FOR KIDNEY STONE DETECTION AND CHARACTERIZATION

CROSS-REFERENCE TO RELATED APPLICATION

This application claims priority under 35 U.S.C. § 119 to U.S. Provisional Application No. 62/680,834, entitled, "Advanced Ultrasound Imaging Techniques for Kidney Stone Detection and Characterization," filed Jun. 5, 2018, the contents of which are incorporated herein by reference.

FIELD OF THE INVENTION

The present invention relates to analyzing kidney stones, and more specifically to systems and methods for determining the true size of kidney stones.

BACKGROUND

Modern lifestyle changes have brought an increase in the prevalence of kidney stone disease, especially in children and young adults. With the increase in the prevalence of kidney stone disease comes increased morbidity, reduced quality of life, and a greater toll on health care resources. Kidney stone prevalence is one in eleven people and the rates are rising. Kidney stone disease has a significant economic impact and is associated with over $5 billion in direct costs in the United States in 2000. Up to 40% of first-time stone formers will have a recurrent event, and up to 10% of stone formers have three or more stone events. Kidney stone problems account for three million annual doctors' visits and half of these visits come from individuals who already had at least one kidney removal.

Proper management of the disease requires accurate detection and sizing in order to determine the burden on the patient and the necessity of surgical intervention. Quickly detecting and accurately sizing kidney stones is important because kidney stones can be extremely painful, and lead to local infection, renal injury, and sepsis.

Conventional processes rely on ultrasound B-mode imaging or computed tomography (CT) to identify and size kidney stones. Although CT can have high sensitivity and specificity, CT is costly and has ionizing radiation exposure. This exposure can contribute towards a future malignancy risk and the exposure is particularly problematic for younger populations. Ultrasounds, on the other hand, are low cost, portable, and has no ionizing radiation risks. However, compared to CT ultrasound, ultrasounds have poorer sensitivity (24-69%) and specificity (82-91%), and tend to overestimate stone widths by 2-3 mm.

This inability to accurately size stones can impose unnecessary burden on doctors and patients alike, since a 5 mm diameter stone is considered a threshold for surgical intervention. Some studies find that 22% of patients receiving exclusively ultrasound for diagnosis were inappropriately counseled, so it is unsurprising that CT is still used in most cases despite the health drawbacks.

Because of ultrasounds' inability to accurately size stones, the acoustic shadow produced by the stone and twinkling artifacts seen with color Doppler have been used as substitutes for conventional imaging for stone sizing and detection. However, often neither a shadow nor a color Doppler artifact are present. Additionally, these sizing methods experience lower sensitivity for stones less than 5 mm. These sizing methods an also experience high false-negative detection rates.

Therefore, a kidney stone imaging technique is needed which can accurately detect and size kidney stones in a subject without exposing the subject to ionizing radiation.

SUMMARY

The various examples of the present disclosure are directed towards a method for detecting and sizing mineralized tissue. The method can comprise a set of steps and can begin with imaging a region of interest containing the mineralized tissue with unfocused ultrasound beams or in unfocused regions of focused ultrasound beams via a primary imaging method. The method can then provide for computing a wavefront coherence at the imaged region of interest. The method can then provide for segmenting pixels of the imaged region of interest based on their intensities and intensities of surrounding pixels. The method can then provide for identifying a border and a shadow of the mineralized tissue based on the segmenting. The method can then provide for calculating a size of the mineralized tissue based on the border and the shadow.

In some examples of the present disclosure, the primary imaging method can comprise first modeling a plurality of sources of image degradation. The primary imaging method can then provide for receiving, at a transducer, the unfocused ultrasound beams. The primary imaging method can then provide for breaking the unfocused ultrasound beams into approximate points of origin. The primary imaging method can then provide for reconstructing ultrasound pressure waves originating only from a particular location in the region of interest.

In other examples of the present disclosure, the primary imaging method can provide for focusing the unfocused ultrasound beams using a transmit synthetic aperture. The primary imaging method can then provide for transmitting the focused ultrasound beams at different angles.

In other examples of the present disclosure, the primary imaging method can provide for calculating a spatial phase from the unfocused ultrasound beams. The primary imaging method can then provide for windowing the unfocused ultrasound beams into a plurality of windows. The primary imaging method can then provide for multiplying each of the plurality of windows by the ultrasound beams. The primary imaging method can then provide for normalizing each of the plurality of windows by a signal energy of the unfocused ultrasound beams. The primary imaging method can then provide for creating a measure of phase based on the normalizing of each of the plurality of windows.

In other examples of the present disclosure, the primary imaging method can provide for acquiring a plurality of angled plane waves. The primary imaging method can then provide for applying a delay to the plurality of angled plane waves. The primary imaging method can then provide for calculating and summing phase images from each of the plurality of angled plane waves. The primary imaging method can then provide for summing coherent measures, summing coherent measures, wherein the summed coherent measures comprise middle lags.

The calculating and summing of phase images can comprise calculating and summing a first set of delays, wherein the first set of delays are a plurality of delays happening closest in time to an initiation of the imaging. Alternatively, the calculating and summing of phase images can comprise calculating and summing a second set of delays, wherein the second set of delays omit any delays happening closest in time to an initiation of the imaging. The second set of delays further can also omit any delays happening farthest in time to an initiation of the imaging.

BRIEF DESCRIPTION OF THE DRAWINGS

The accompanying drawings exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

FIG. 21A shows ultrasound simulations with varying stone surface roughness, according to various embodiments of the present disclosure.

FIG. 21B shows the change in B-mode image power as a function of roughness, according to various embodiments of the present disclosure.

DETAILED DESCRIPTION

Figure 1A:
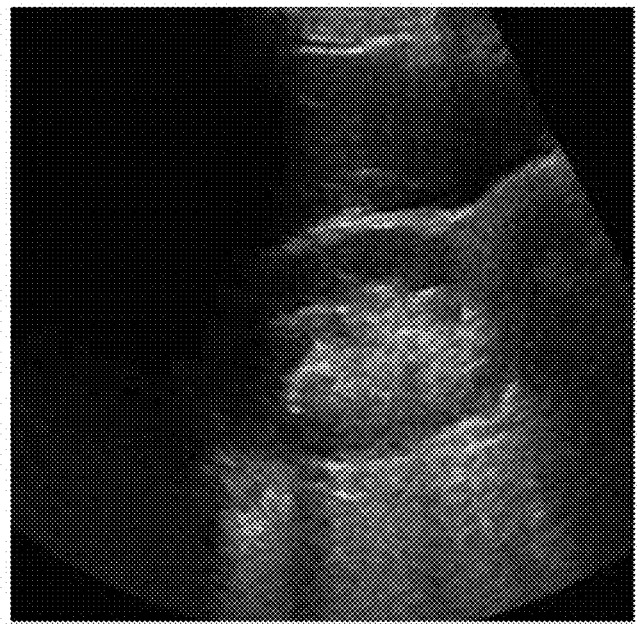
FIG. 1A shows an example of ultrasound imaging on a kidney stone, according to a conventional imaging method.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

The present disclosure is directed towards discussing five various methods of detecting kidney stone sizes. The five methods include (1) the conventional B-mode (B-mode) method as used in the prior art, (2) the Plane Wave Synthetic Focusing (PWSF) method, (3) the Aperture Domain Model Image Reconstruction (ADMIRE) method, (4) the Short-lag Spatial Coherence (SLSC) method, and (5) the Mid-lag Spatial Coherence (MLSC) method with incoherent compounding. ADMIRE and SLSC are both designed to handle reverberation and multipath scattering to improve image quality, and MLSC seeks to enhance coherent scatterers (e.g. stones) while suppressing other signals. PWSF was implemented with angled plane wave transmit beams as a form of synthetic aperture imaging. These methods are discussed further with respect to FIGS. 2-6B.

Soft tissues, such as kidneys, provide incoherent wavefronts and hard mineralizations, such as kidney stones, provide coherent wavefronts. Conventional imaging techniques induce coherence so that tissues and hard structures look similar. The present disclosure intentionally avoids inducing coherence in soft tissue by using unfocused ultrasound beams to make images of wavefront coherence. This method thus can be applied to any task where mineralized tissue is of interest, including kidney stones, gall stones, breast microcalcifications, and/or cardiovascular calcifications.

FIG. 1A shows an exemplary ultrasound B-mode imaging technique according to the prior art. FIG. 1A shows that the imaging cannot accurately or clearly identify the location of any kidney stone. Furthermore, FIG. 1A shows the futility of attempting to size a kidney stone at all, much less accurately size the kidney stone. Additionally, FIG. 1A shows that when an acoustic shadow and stone twinkling are absent, the kidney stone cannot be identified and sized via ultrasound techniques.

Figure 1B:
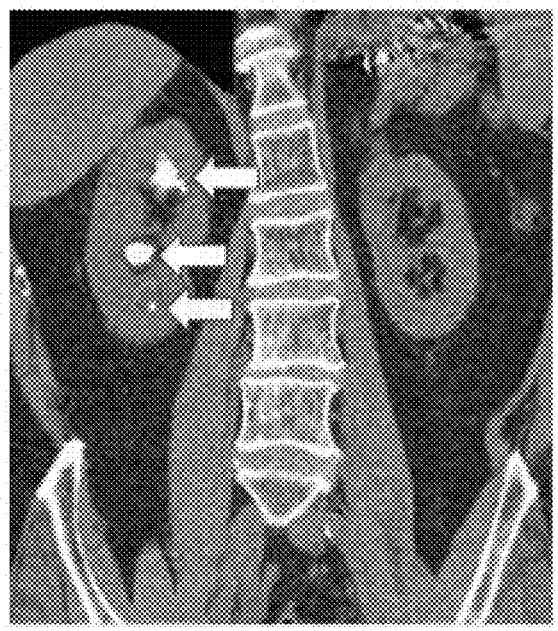
FIG. 1B shows an exemplary CT scan of a set of kidney stones, according to a conventional imaging method.

FIG. 1B shows an exemplary CT scan imaging technique for a set of in vivo kidney stone according to the prior art. FIG. 1B shows that CT scans can accurately identify and clearly size kidney stones through easy identification of the white spots on the scan. Three arrows point to three locations of different kidney stones. Although CT scans provide good visibility and sizing for kidney stones, CT scans expose subjects to ionizing radiation and are expensive.

Figure 2:
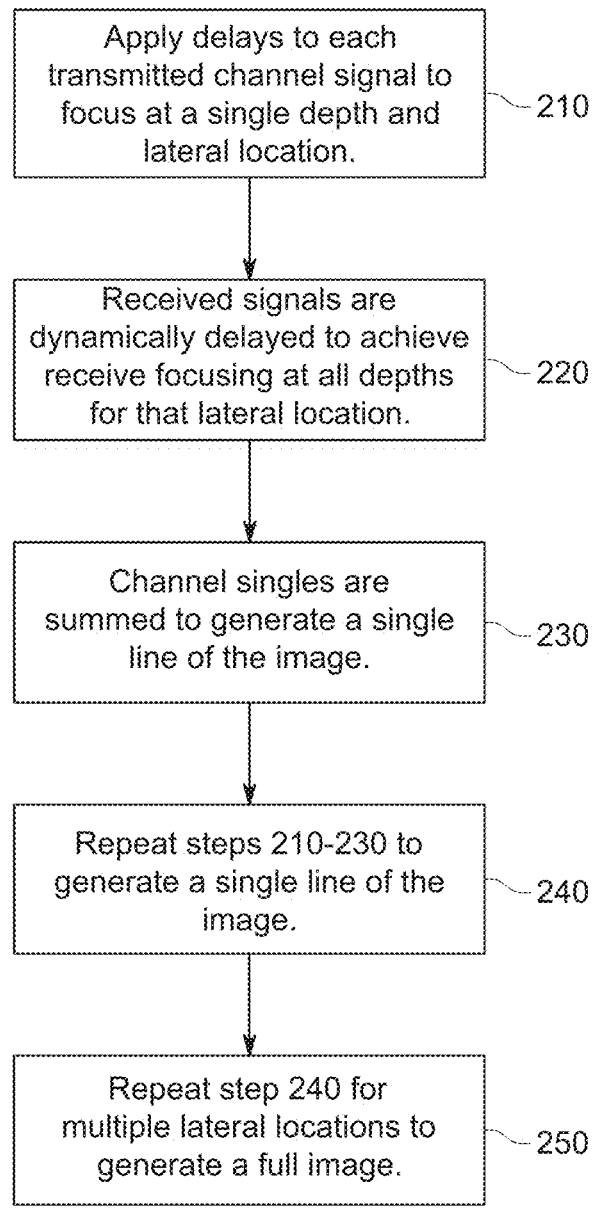
FIG. 2 is a flowchart of an exemplary B-mode imaging technique, according to a conventional imaging method.

FIG. 2 shows an exemplary method 200 of a B-mode imaging technique according to the prior art. The method can be performed by a computing system on a sample of interest. The sample can be a human organ or an experimental set-up. At step 210, the computing system can apply delays to a transmitted channel signal. The transmitted channel signal will focus at a single depth and lateral location in the sample of interest. In step 220, the signals can be received and then dynamically delayed to achieve receive focusing at all depths in the sample of interest for that lateral location. In step 230, the channel signals can be summed to generate a single line of the image. Step 240 can provide for repeating steps 210-230 to generate a single vertical line of an image for the sample of interest. Step 250 can repeat step 240 in turn for multiple lateral, or horizontal locations. The completion of method 200 can generate a full image. The overall process has been also referred to as delay-and-sum beamforming (DAS).

The B-mode imaging technique has limitations through its inability to focus at multiple depths. These limitations make it difficult to identify and properly size a kidney stone by using just B-mode imaging. This is further demonstrated in FIG. 1A.

Figure 3:
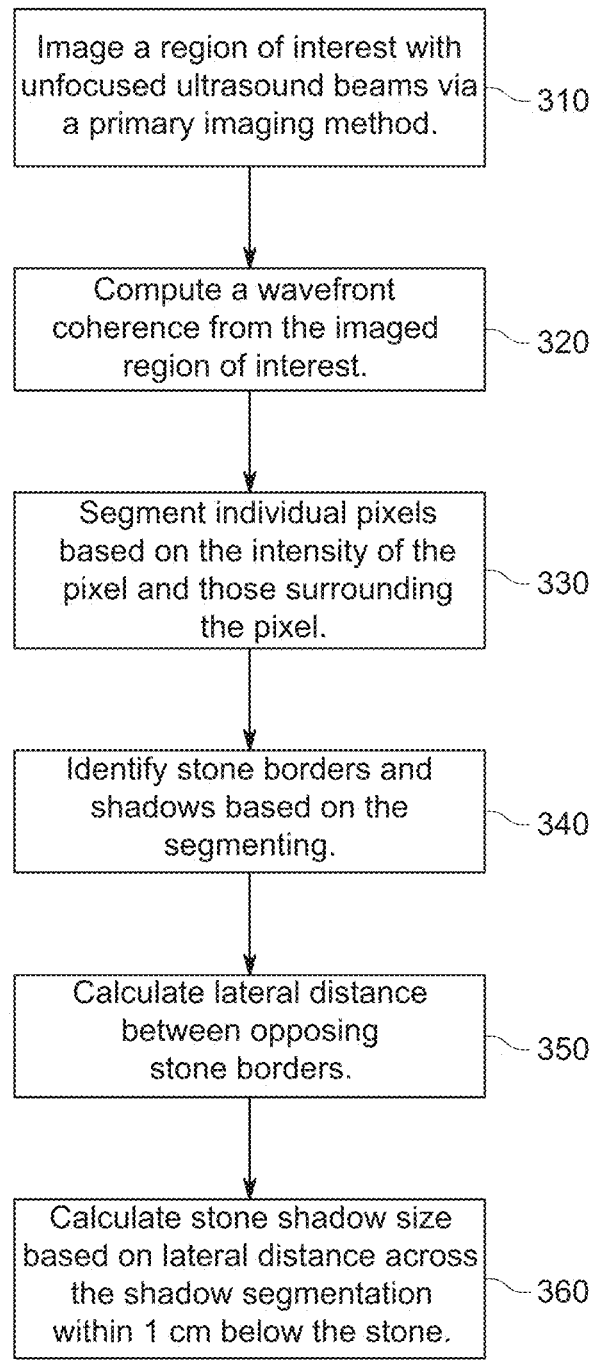
FIG. 3 is a flowchart of an exemplary kidney stone detection and sizing methodology, according to an embodiment of the present disclosure.

FIG. 3 is a flowchart of an exemplary method 300 for detecting and sizing kidney stones. The method can be performed by a computing system on a sample of interest. The sample can be a human organ or an experimental set-up. The system can begin at step 310 by imaging a region of interest with unfocused ultrasound beams or in unfocused regions of focused ultrasound beams via a primary imaging method. Exemplary primary imaging techniques can be discussed further with respect to FIGS. 4-6A.

In some examples, imaging of the region of interest is performed by any medical ultrasonography imaging methods, as known in the art. For example, a general-purpose ultrasound transducer or a specialty transducer is used on the surface of a patient's body. In some examples, a transducer is placed inside the body. In some examples, the ultrasound imaging is performed by emitting a beam of sound waves, via the transducer, directed at the region of interest. The sound waves are transmitted through the patient's body and then bounce back. The transducer collects sound waves that bounce back and then creates an image based on the characteristics of the sound waves.

In various embodiments of the present disclosure, the beam is focused or unfocused. In an unfocused beam, the beam diverges from the near field path, yielding the far field after the focal point. In an unfocused beam, the resolution is best viewed in the near field. In a focused beam, the beam's narrowest point is a narrow area of high resolution, referred to as the focal zone. When imaging, narrow beams provide an unfocused region outside of the focal zone. Therefore, focused beams are only focused within a limited depth range, and, outside of that focused region, the beams are unfocused.

Therefore, in some examples of the present disclosure, imaging of the region of interest is performed on a patient by ultrasonography imaging methods as known in the art. In other examples of the present disclosure, imaging of the region of interest is performed on ultrasonography imaging data.

Referring back to FIG. 3, the system can then compute a wavefront coherence from the imaged region of interest at step 320. In some examples of step 320, the images of wavefront coherence can be noisy because measures of coherence are stochastic so occasionally even soft tissue appears coherent. Step 320 can provide for additionally averaging independent realizations of speckle together in order to reduce the variability of the underlying stochastic process.

In some examples of step 320, coherence is determined based on the ultrasonography data collected at step 310. Coherence describes all properties of the correlation between physical quantities of a single wave, or between several waves or wave packets, including, for example, phase difference, frequency, and waveform characteristics of one or more waves (e.g., the focused or unfocused beams sent by an ultrasound transducer).

For example, coherence is estimated for different levels of spacing between the ultrasound channel data at different degrees of spacing across the elements of the transducer array. This produces a 'coherence curve' for each pixel in the image of step 310. In some examples, the middle values of the curve are summed together to produce one pixel, yielding an image of the endogenous coherence in the tissue. In other words, if using a Verasonics Vantage 128 transducer with a 128-element array probe, the steps could include: 1.) Imaging the tissue with an unfocused beam at multiple angles and collecting the channel data from the ultrasound system. 2.) Computing a wavefront coherence value from the data, omitting the first few short lags with spacing closest to the reference element (for example lag 1, lag 2, etc.), summing up the middle lags (e.g. lag 4-15), and omitting the long lags (e.g. lag 16 to 128). 3.) Repeat step 2 for the data from each unfocused beam. 4.) Sum the unfocused beams together.

In some examples of step 320, the coherence is determined based on a physics-based model of the wave propagation from signal sources and noise sources. For example, the channel data is fit using an elastic-net regularization constraint to separate the signal and noise. An image is then created by reconstructing the signal portion without the noise.

In step 330, the system can segment individual pixels. The segmenting can be based on an intensity of each pixel and intensities of a plurality of nearby pixels. For example, the pixels are the pixels in the image created at step 310. In some examples, the pixels are the pixels created in an image according to the various embodiments discussed above with respect to step 320.

In some examples of steps 320 and 330, the present disclosure provides for summing coherence images acquired from ultrasonography data at different angles. The coherence images are calculated only from the middle lags, omitting the beginning lags and the ending lags (as discussed further herein with respect to FIGS. 11-13B).

In step 340, the system can then identify the borders of the stone and the stone shadows based on the segmenting. In step 350, the system can then calculate a lateral distance between opposing stone borders. This calculation can determine a size of the stone.

In step 360, the system can calculate a size of the stone shadow based on a lateral distance across the shadow. The lateral distance can be located within one cm below the stone. The size of the stone shadow can provide additional or supplementary information on the size of the kidney stone.

In some examples of the present disclosure, an automated segmentation algorithm implemented in MATLAB was used to identify stone borders and shadows. The method segments individual pixels iteratively by assigning them to classes based on the intensity of the pixel and those surrounding it. With minimal additional user input, the stone and shadow can be quickly segmented, allowing for greater consistency and accuracy compared to manual sizing methods.

The contrast of the stone relative to the gelatin and the contrast of the shadow relative to the gelatin can be calculated for each stone and method using the following formulas:

$$\text{contrast stone} = 20 \log 10(\mu\text{stone}/\mu\text{gel}) \quad \text{(Equation 1)}$$

$$\text{contrast shadow} = 20 \log 10(\mu\text{shadow}/\mu\text{gel}) \quad \text{(Equation 2)}$$

where $\mu$ is the mean intensity of the stone, shadow, or gelatin background.

Stone sizing can be calculated as the lateral distance across the stone segmentation described prior, and the shadow size was determined as the lateral distance across the shadow segmentation within 1 cm below the stone.

PWSF is one exemplary primary imaging method that can be used in step 310 of the method 300. PWSF focuses on all depths using a transmit synthetic aperture. Transmit synthetic aperture focusing enables ultrasound systems to create synthetic transmit focuses throughout the image much like modern systems all utilize dynamic receive focusing to focus everywhere on the receive signal. According to the present disclosure, PWSF relies on transmitting plane waves at different angles. PWSF is superior to conventional B-mode imaging because it achieves transmit focusing at all depths instead of at just a single depth.

Figure 4:
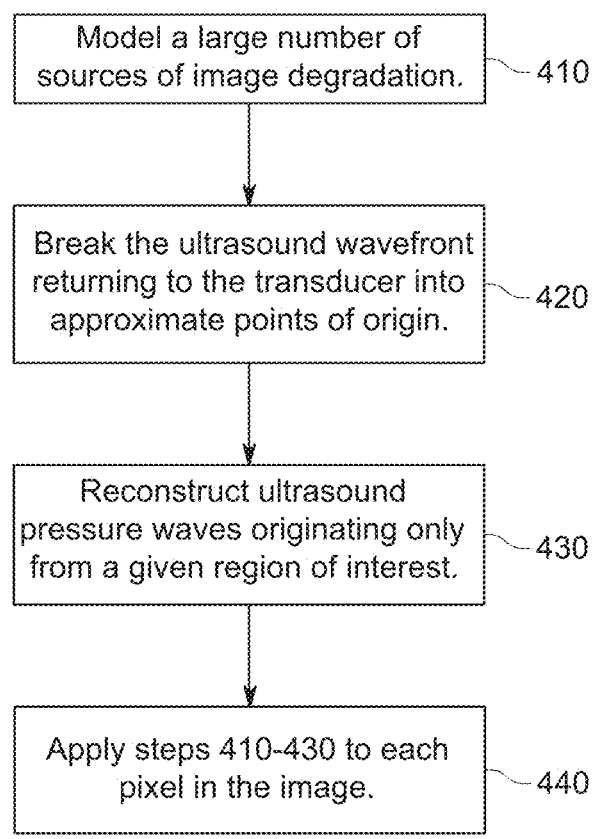
FIG. 4 is a flowchart of an exemplary Aperture Domain Model Image Reconstruction method, according to an embodiment of the present disclosure.

FIG. 4 shows another exemplary primary imaging technique 400 that can be used in conjunction with method 300. FIG. 4 shows a method 400 based on ADMIRE. ADMIRE makes use of the physics of linear ultrasound wave propagation and the effect of various sources of image degradation. The method can be performed by a computing system on a sample of interest. The sample can be a human organ or an experimental set-up.

Sources of image degradation can be bright sources (i.e. stones) or reverberant sources such as those coming from shallow fat and muscle tissue. The method 400 can begin in step 410 by modeling a large number of these sources of image degradation. In step 420, the ultrasound wavefront returning to the transducer at a given time can be broken down into approximate points of origin. In step 430, ultrasound pressure waves originating only from a given region of interest can be reconstructed into a high-quality B-Mode signal. In step 440, steps 410-430 can be applied to each pixel in the image. In some embodiments of the present disclosure, ADMIRE can be implemented alongside PWSF.

Figure 5A:
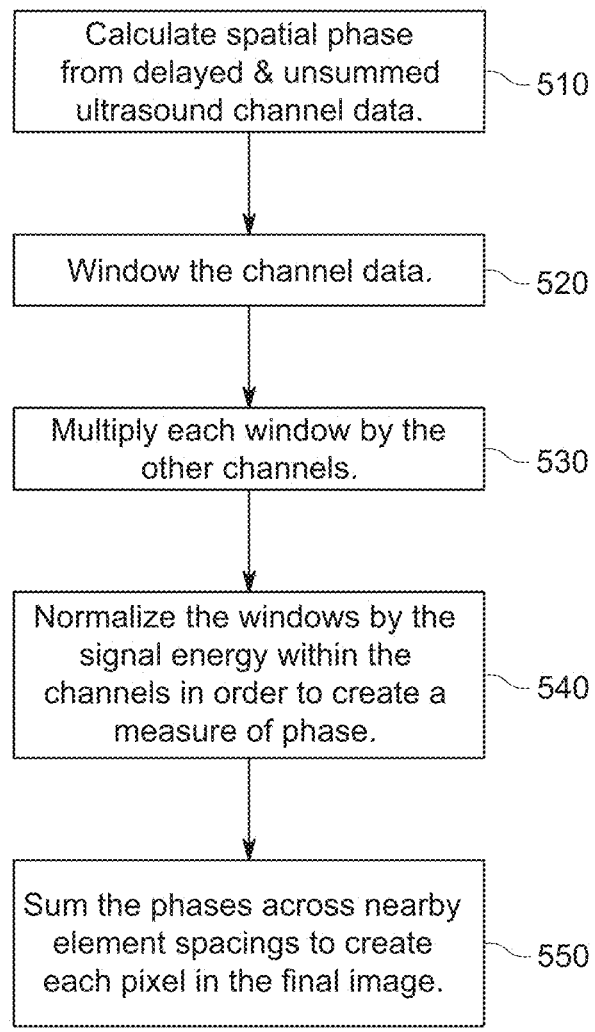
FIG. 5A is a flowchart of a Short-lag Spatial Coherence (SLSC) method, according to an embodiment of the present disclosure.

FIG. 5A shows a flowchart of an exemplary SLSC method 500 according to an embodiment of the present disclosure. The method 500 can be performed by a computing system on a sample of interest. The sample can be a human organ or an experimental set-up.

In step 510, the computing system can initiate the SLSC by calculating a spatial phase from the delayed and pre-summed ultrasound channel data. In step 520, the channel data can be windowed. This preserves axial resolution. In step 530, each window can be multiplied by the other channels. In step 540, the windows can be normalized by the signal energy within the channels in order to create a measure of phase (i.e. coherence). In step 550, the phases across nearby element spacings can be summed to create each pixel in a final image.

SLSC can create images correlated with a spatial phase of the ultrasound wavefronts across the surface of a transducer. In some embodiments of the present disclosure, SLSC can be combined with PWSF to increase the depth of field. SLSC can improve image quality in a range of scenarios. SLSC is also particularly suited to imaging difficult to image patients where image degradation is known to be a problem. Additionally, SLSC can eliminate random instances of apparently, but not actually, coherent media (noise).

Figure 5B:
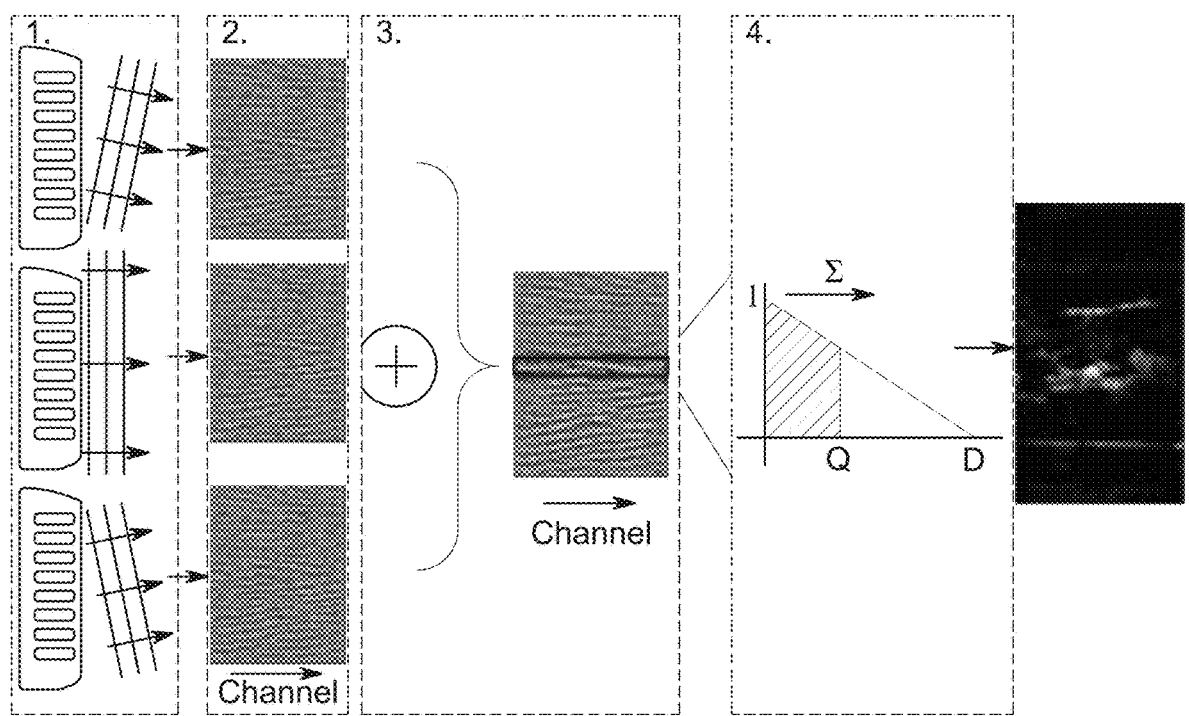
FIG. 5B shows a diagram of an exemplary SLSC method, according to an embodiment of the present disclosure.

FIG. 5B shows a diagram of an exemplary SLSC method according to an embodiment of the present disclosure. For example, box one demonstrates the angles of various plane waves. Box two demonstrates the application of delays to the angled plane waves. Step 3 demonstrates the summation of the angled plane waves. Box 4 demonstrates how normalization can occur for only delays happening closest in time to an initiation of the imaging.

Figure 6A:
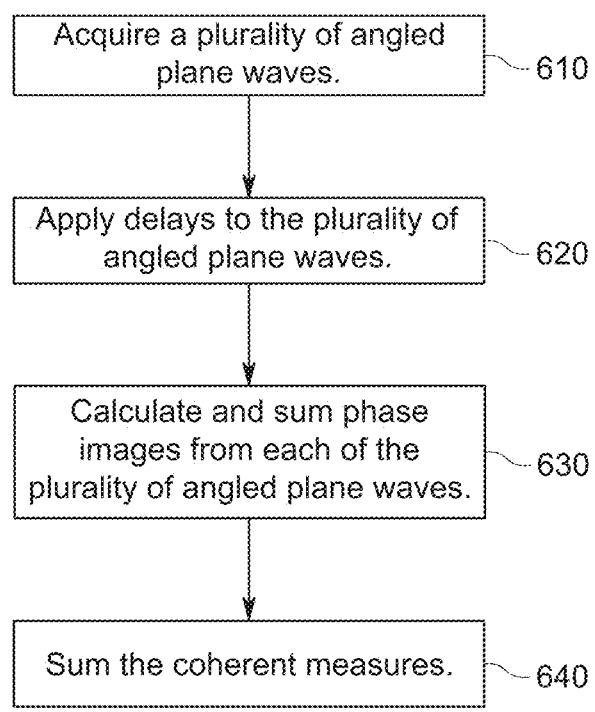
FIG. 6A is a flowchart of the Mid-lag Spatial Coherence (MLSC) method, according to an embodiment of the present disclosure.

FIG. 6A shows a flowchart of an exemplary MLSC method 600 according to an embodiment of the present disclosure. MLSC is similar to SLSC but the order of the processing steps is rearranged to preferentially suppress the signal from tissue. To this end, MLSC performs the spatial phase quantification used with SLSC but before transmit beamforming. This means that there is no introduction of phase by the transmit beamforming as occurs in SLSC. The method 600 can be performed by a computing system on a sample of interest. The sample can be a human organ or an experimental set-up.

Method 600 begins in step 610 where the computer system can acquire angled plane waves. In step 620, the method can then apply delays to the angled plane waves. In step 630, the method can calculate and sum a phase image from each of the plurality of angled plane waves. In step 640, the method can then sum the coherent measures in order to enhance the stone and suppress any random correlations in the tissue.

Similar to SLSC, MLSC can be implemented with PWSF. Additionally, because spurious points of coherence that may occur will occur in the shortest lags, the shortest lags can be excluded from the sum used to create the phase image from each of the plurality of angled plane waves. The ability of MLSC to suppress everything except for the stone both in in vitro and ex vivo cases demonstrates promise in stone detection and sizing. Therefore, MSLC provides calculation of the coherent images from the middle lags.

Figure 6B:
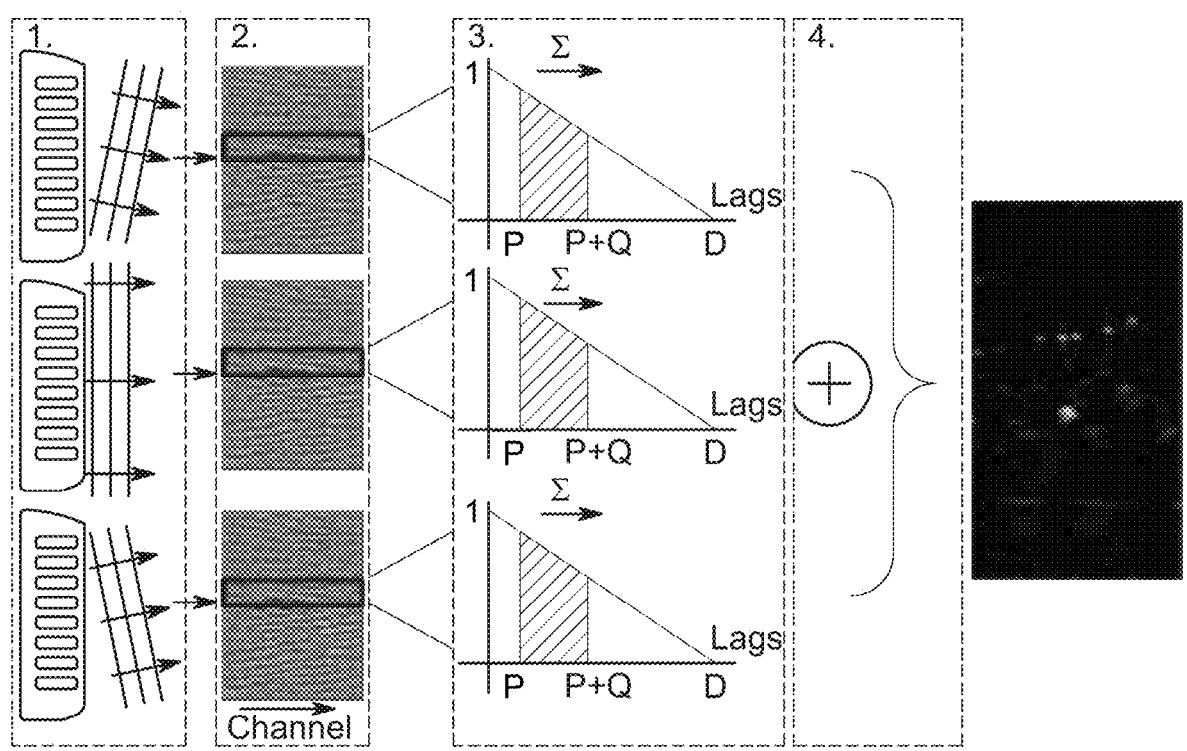
FIG. 6B shows a diagram of an exemplary MLSC method, according to an embodiment of the present disclosure.

FIG. 6B shows a diagram of an exemplary MLSC implementation according to an embodiment of the present disclosure. Box 1 demonstrates the angles of various plane waves. Box 2 demonstrates the application of delays to the angled plane waves. Step 3 demonstrates the summation of the angled plane waves. Box 3 demonstrates how normalization can occur for only delays in a mid-time region. Box 4 demonstrates the summation of the angled plane waves. In other words, the delays omit any delays happening closest in time to an initiation of the imaging or any delays happening closest in time to a conclusion of the imaging.

Experimental Results

In one example, a Verasonics Vantage 128 system with an L7-4 linear array transducer was used to detect kidney stones. The system attempted to detect eight human calcium-based kidney stones. The eight stones had a mean size of 9.88 mm with a range of between 2 and 18 mm. The stones were placed on top of graphite-embedded gelatin phantoms, which served as a platform and provided a diffuse scattering background for comparisons. Stones were rehydrated and degassed for at least 24 hours before being placed on a graphite-embedded gelatin phantom immersed in a water bath for imaging. The transducer was submerged in the water bath and images were acquired with the stone at 4 cm and 8 cm depths. PWSF was acquired at 1° increments from −30° to 30° at a center frequency of 5.2 MHz. Data was processed in MATLAB (Natick, WA) and sound speed was assumed to be 1480 m/s.

The stones were first measured with PWSF. ADMIRE, SLSC, and MLSC were applied afterwards for additional beamforming. After data processing for each method, an automated segmentation algorithm implemented in MATLAB was used to identify stone borders and shadows. As discussed with respect to step 360 of FIG. 3, the method can segment individual pixels iteratively by assigning them to classes based on the intensity of the pixel and those surrounding it. A contrast of the stone relative to the gelatin and the contrast of the shadow relative to the gelatin can be calculated for each stone and method using Equation 1 and Equation 2 as discussed with respect to FIG. 3.

Figure 7A:
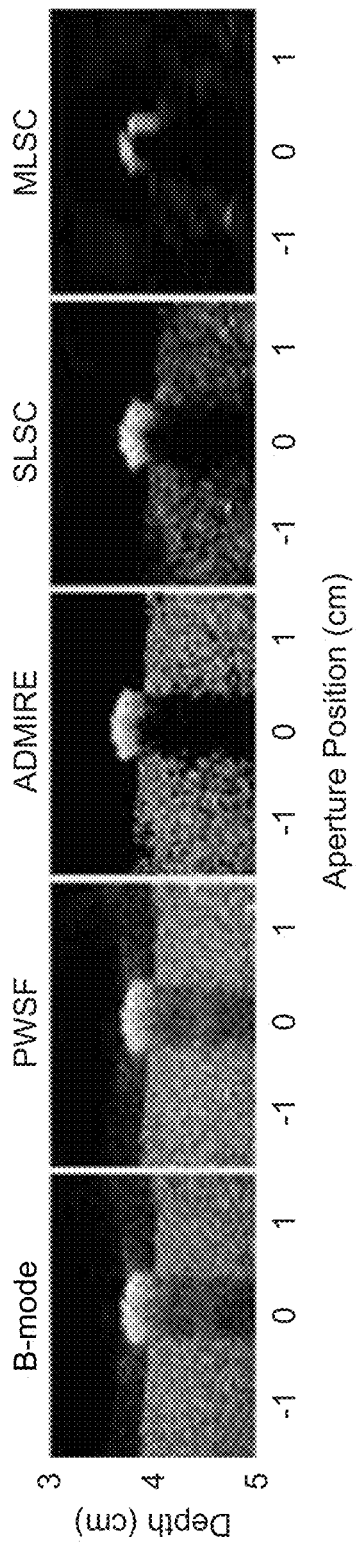
FIG. 7A shows a comparison of various methods of detecting and sizing kidney stones when evaluating a stone at a depth of 4 cm, according to an embodiment of the present disclosure.
Figure 7B:
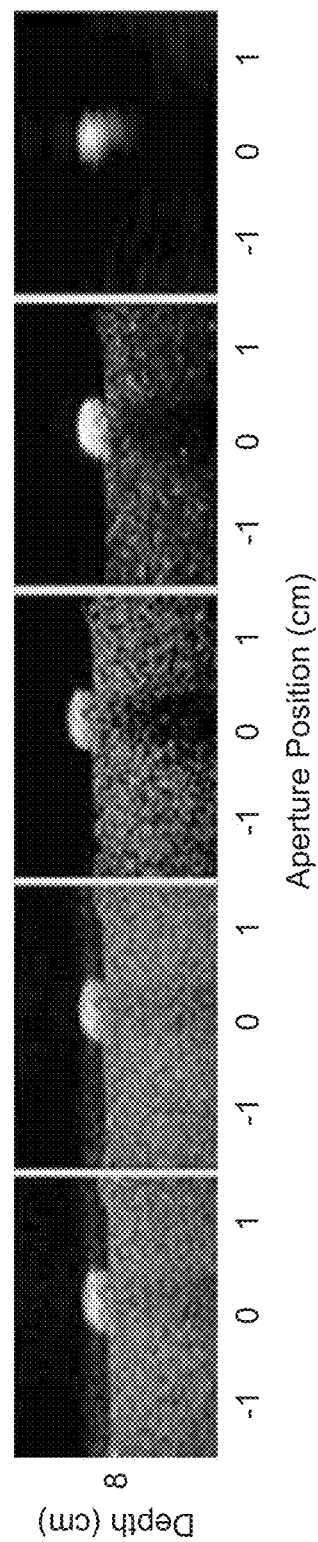
FIG. 7B shows a comparison of various methods of detecting and sizing kidney stones when evaluating a stone at a depth of 8 cm, according to an embodiment of the present disclosure.

FIG. 7A-B shows the experimental results of imaging a kidney stone in vitro as compared between the various imaging techniques. FIG. 7A shows images of an 8 mm stone in vitro at a depth of 4 cm. FIG. 7A shows that MLSC performs best at sizing stones accurately at 4 cm. The significant MLSC results for stone contrast compared to B-mode echo what was observed in the in vitro and ex vivo images, further supporting the notion that MLSC could be an ideal technique for stone detection.

FIG. 7B shows images of the 8 mm stone in vitro at a depth of 8 cm. FIG. 7B shows that ADMIRE sizes stones more accurately at deeper depths and performs best overall across all depths. ADMIRE, and SLSC to a lesser extent, show improvements in increasing the contrast of the stone shadow. At deeper depths, the differences between ADMIRE and the conventional B-mode method were especially obvious, meaning it may be the best for characterizing the shadow FIGS. 7A-B show that PWSF and SLSC both perform better than the conventional B-mode method.

Sizing accuracy was determined by analyzing the error (measurement error=segmented size−true size). Mean measurement errors were calculated for each beamforming method at 4 cm, 8 cm, and overall. Likewise, stone and shadow contrasts were compared between methods. Analysis of variance was used to find differences among the methods, with p<0.05 considered significant. A t-test can be used to compare methods according to various embodiments of the present disclosure with the B-mode method of the prior art. The t-test can identify results with a Bonferroni corrected significance level of p<0.0025. The in vitro sizing errors for all stones at both depths for PWSF, ADMIRE, SLSC, and MLSC is shown below in Table 1. FIGS. 8A-B shows that ADMIRE performs best in vitro for sizing. Table 2 shows shadow sizing errors in millimeters as compared across B-mode ADMIRE, SLSC, and MLSC. Table 3 shows measurements of stone contrast relative to B-mode. Table 4 shows shadow contrast relative to B-mode. All values in Tables 1-4 which are represented with an asterisk have a significance value with ANOVA at p<0.0025.

TABLE 1

Stone sizing error in millimeters

| Depth | B-model | PWSF | ADMIRE | SLSC | MLSC |
|---|---|---|---|---|---|
| 4 cm | Ref | 1.8 ± 1.2 | 1.0 ± 0.9 | 0.8 ± 0.8 | 1.0 ± 1.1 |
| 8 cm | Ref | 1.1 ± 0.9 | 0.8 ± 0.6 | 0.4 ± 0.6 | 1.0 ± 1.6 |
| All | Ref | 1.4 ± 1.1 | 0.9 ± 0.7 | 0.6 ± 0.7 | 1.0 ± 1.3 |

TABLE 2

Shadow sizing error in millimeters

| Depth | B-mode (mm) | PWSF (mm) | ADMIRE (mm) | SLSC (mm) | MLSC (mm) |
|---|---|---|---|---|---|
| 4 cm | −1.3 ± 1.3 | −1.6 ± 1.5 | −0.7 ± 0.9 | 1.0 ± 1.6 | — |
| 8 cm | −2.5 ± 0.9 | −2.1 ± 1.0 | −2.7 ± 3.7 | 0.4 ± 3.3 | — |
| All | −1.7 ± 1.3 | −1.8 ± 1.3 | −1.5 ± 2.4 | 0.8 ± 2.4 | — |

TABLE 3

Stone Contrast Relative to B-mode (dB)

| Depth | B-model | PWSF | ADMIRE | SLSC | MLSC |
|---|---|---|---|---|---|
| 4 cm | Ref | −0.5 ± 2.6 | 3.2 ± 3.6 | −5.7 ± 2.6 | 26.8 ± 10.0* |
| 8 cm | Ref | −1.5 ± 1.9 | 3.2 ± 2.4 | −5.2 ± 4.9 | 13.4 ± 6.4* |
| All | Ref | −1.0 ± 2.3 | 3.2 ± 2.0 | −5.4 ± 3.8* | 20.1 ± 10.7* |

TABLE 4

Shadow Contrast Relative to B-mode (dB)

| Depth | B-model | PWSF | ADMIRE | SLSC | MLSC |
|---|---|---|---|---|---|
| 4 cm | Ref | 1.7 ± 0.6 | 19.7 ± 9.5* | 10.2 ± 18.1 | — |
| 8 cm | Ref | 0.3 ± 1.2 | 6.3 ± 5.3 | 3.2 ± 7.7 | — |
| All | Ref | 1.0 ± 1.2 | 13.0 ± 10.2* | 5.6 ± 11.8* | — |

Figure 8:
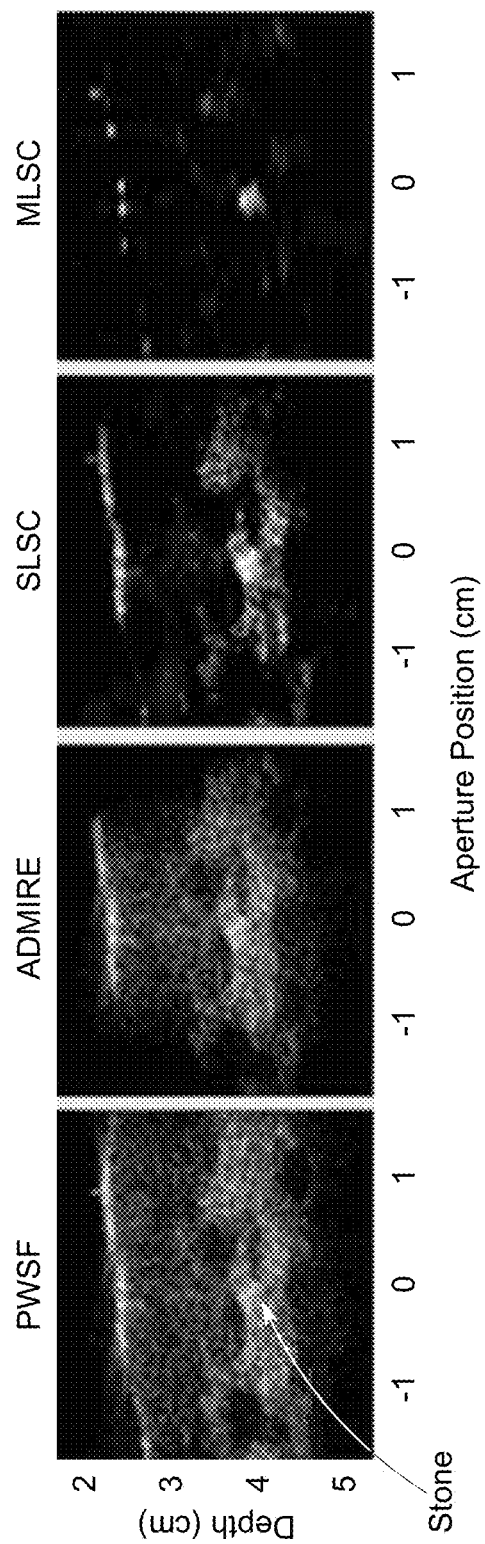
FIG. 8 shows a comparison of various methods of detecting and sizing kidney stones when evaluating a stone placed in a pig kidney, according to an embodiment of the present disclosure.

In another example of the present disclosure, a 10 mm stone was implanted ex vivo into a pig kidney. The pig kidneys were then immersed in water for imaging. FIG. 8 compares the sizing and detection results of PWSF, ADMIRE, SLSC, and MLSC as they reveal and size the kidney stone. A similar procedure was used to detect and size the 10 mm stone in the pig kidney as was used for the 8 mm stones in the in vitro procedure discussed above with respect to FIGS. &A-B. FIGS. 7A-8 shows that although ADMIRE performed best in vitro, the ex vivo study delination of the border was unclear. Instead, MLSC achieved excellent discrimination between the stones and the diffuse scattering media with a constant threshold across all sets ex vivo.

All stones were detectable in vitro with each method, though often difficult to detect ex vivo with B-mode and PWSF. MLSC performed best at stone sizing at 4 cm, but ADMIRE performed best at 8 cm and overall (Table 1, FIGS. 7A-B). Only MLSC at 4 cm was considered significantly different compared to B-mode, though overall PWSF, ADMIRE, and MLSC had errors on average of less than 1 mm and B-mode on average had errors greater than 1 mm.

Shadows were generally detectable for larger stones in vitro, but for stones less than 5 mm there was often no detectable shadow using any method. With MLSC, the shadow was indistinguishable from the gelatin background in almost all cases since the technique suppresses the gelatin. On average, B-mode, PWSF, and ADMIRE all underestimated the stone size based on the shadow width, whereas SLSC overestimated (Table II, FIG. 8).

Stone contrast saw a significant improvement in MLSC at all depths compared to B-mode, while overall SLSC saw a significant decrease in contrast compared to B-mode (Table III, FIG. 7A-B). Generally, ADMIRE and MLSC improved stone contrast. Shadow contrast was significantly improved in ADMIRE at 4 cm and overall compared to B-mode, and PWSF and SLSC saw slight improvements in contrast (Table IV, FIG. 8). In MLSC the gelatin was indistinguishable from the shadow.

In the ex vivo experiment (FIG. 8), the stones were difficult to identify with PWSF and ADMIRE, but in SLSC and MLSC the stones were easy to identify. Subjectively, MLSC suppressed nearly the entire background, making stone identification trivial.

Altogether, the results of estimating the stone width based on the shadow width were unexpected. For stone sizing, B-mode, PWSF, ADMIRE, and SLSC overestimated the stone size on average, but for shadow sizing, B-mode, PWSF, and ADMIRE all underestimated the stone size. On average SLSC continued to overestimate and MLSC was completely unable to detect a shadow for measurements in any cases. These results can therefore lead to more accurate estimates if used in conjunction with the standard stone sizing.

Figure 9:
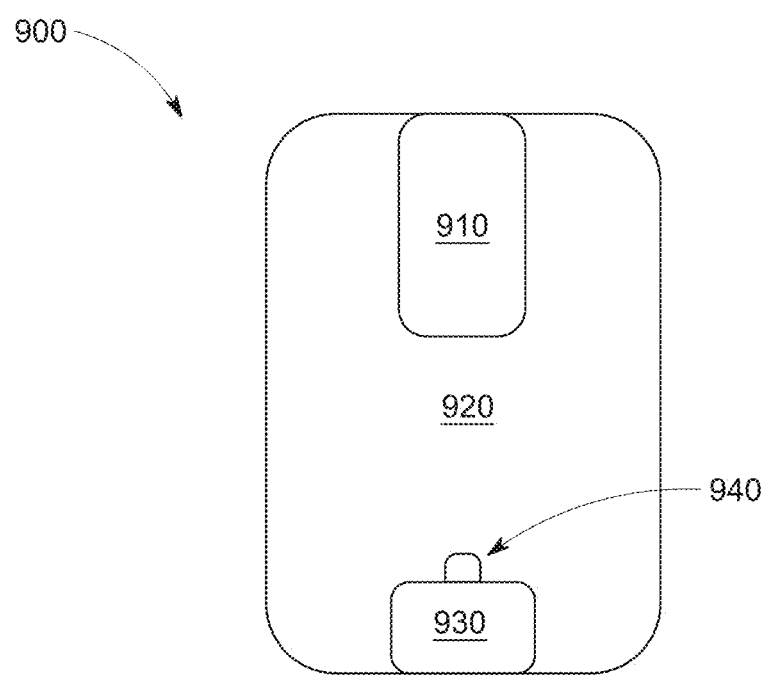
FIG. 9 shows an exemplary system for testing detection and sizing methods, according to an embodiment of the present disclosure.

FIG. 9 shows a system 900 which includes a transducer 910, a containing element 920, a gelatin stand 930, and a kidney stone 940. The transducer 910 can apply the waveform elements to the kidney stone 940. An experimental method can be applied to measure the size of the kidney stone 940 as discussed with respect to FIGS. 7A-8.

Figure 10A:
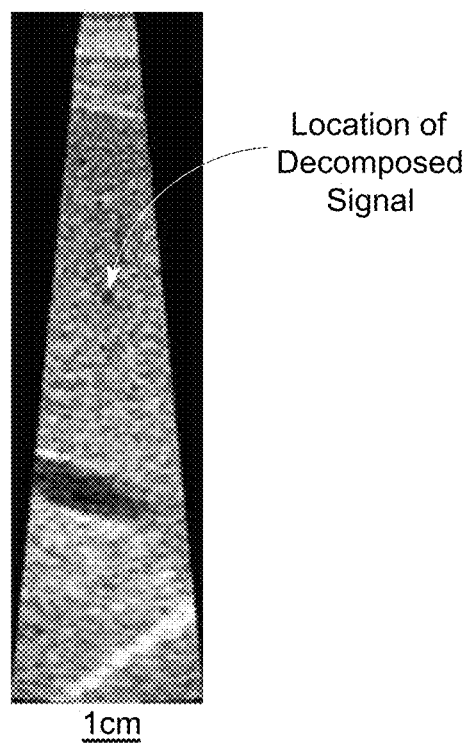
FIG. 10A shows an exemplary image measured, according to an embodiment of the present disclosure.
Figure 10B:
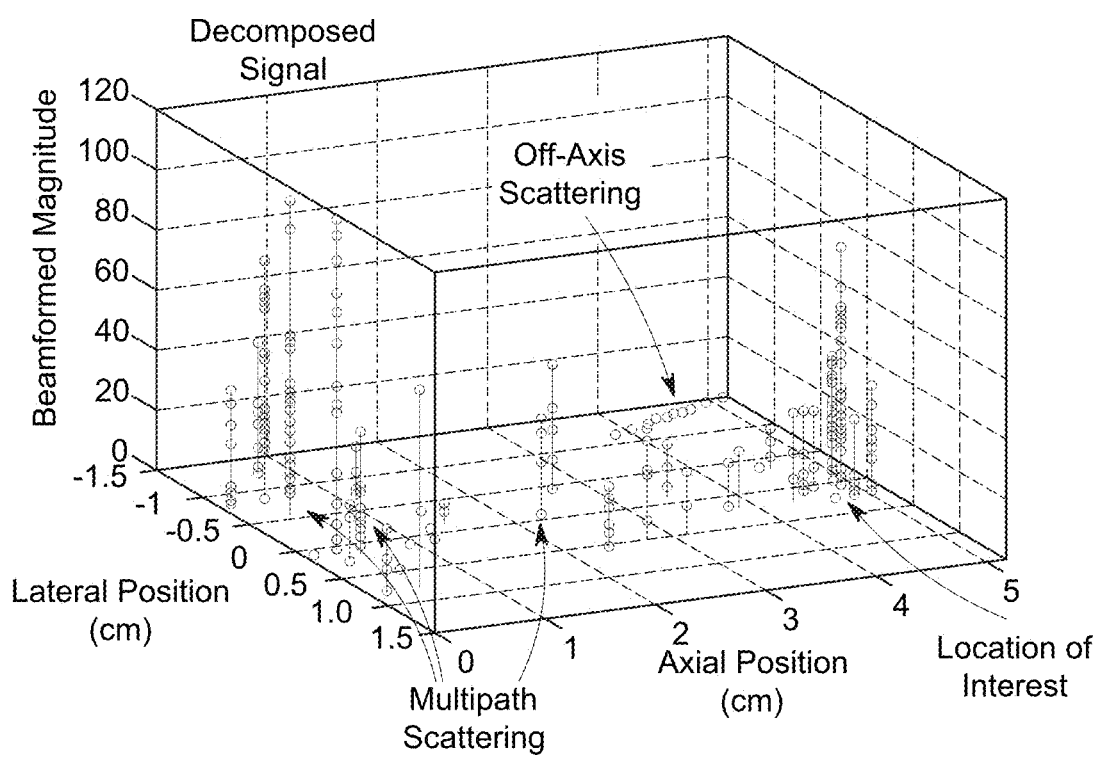
FIG. 10B shows an exemplary decomposed signal measured, according to an embodiment of the present disclosure.

FIG. 10A shows an image measured by the ADMIRE method according to an embodiment of the present disclosure. FIG. 10A shows the ADMIRE method identifying the spatial distribution of energy. FIG. 10B shows a reconstruction of the energy of interest according to the ADMIRE method. The ADMIRE method can detect the decomposed signal and analyze multipath scattering, off-axis scattering, and a location of interest.

Figure 11:
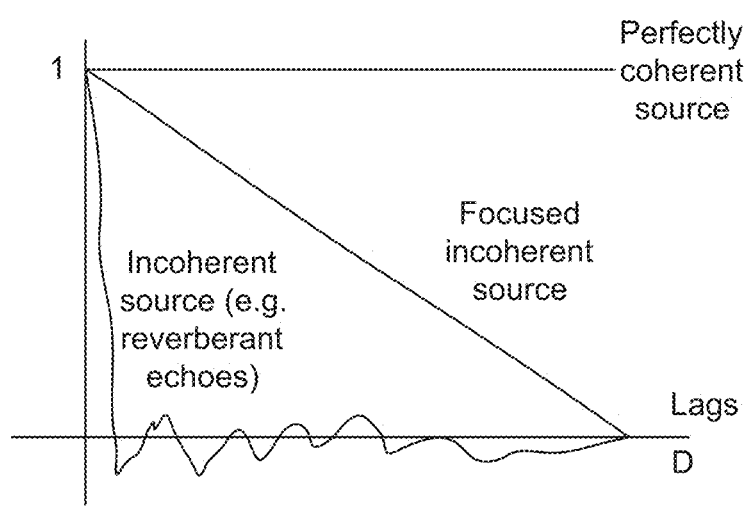
FIG. 11 shows a comparison of the waveforms generated, according to an embodiment of the present disclosure.

FIG. 11 compares the potential lags of different sources. For example, a perfectly coherent source can be a straight line. A focused incoherent source can fall in a linear fashion. An incoherent source can demonstrate reverberant echoes.

Figure 12:
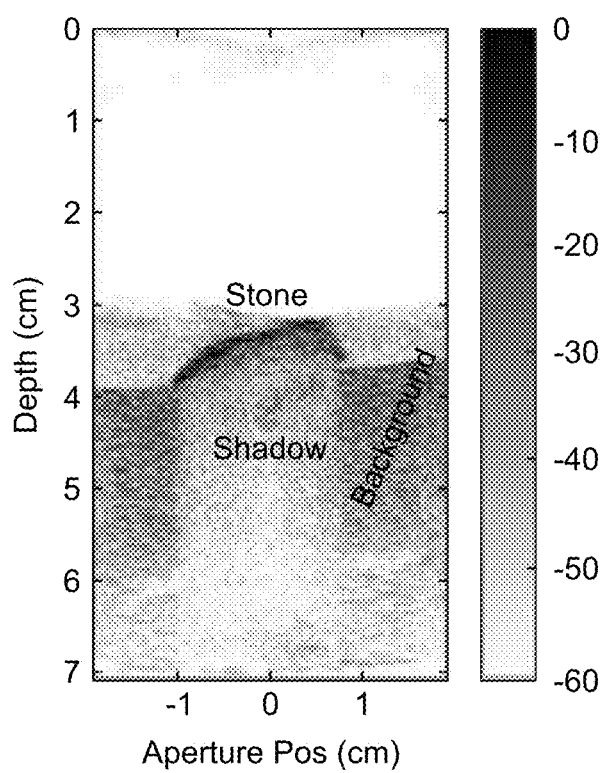
FIG. 12 shows an image of a kidney stone in accordance with an embodiment of the present disclosure.

FIG. 12 shows an exemplary ultrasound image constructed according to an embodiment of the present disclosure. This image shows that the stone can be measured against the background contrast. The background contrast can be measured against the shadow contrast. The stone width can be measured from a lateral length of the stone. The shadow width can be measured from a lateral width of the shadow.

Figure 13A:
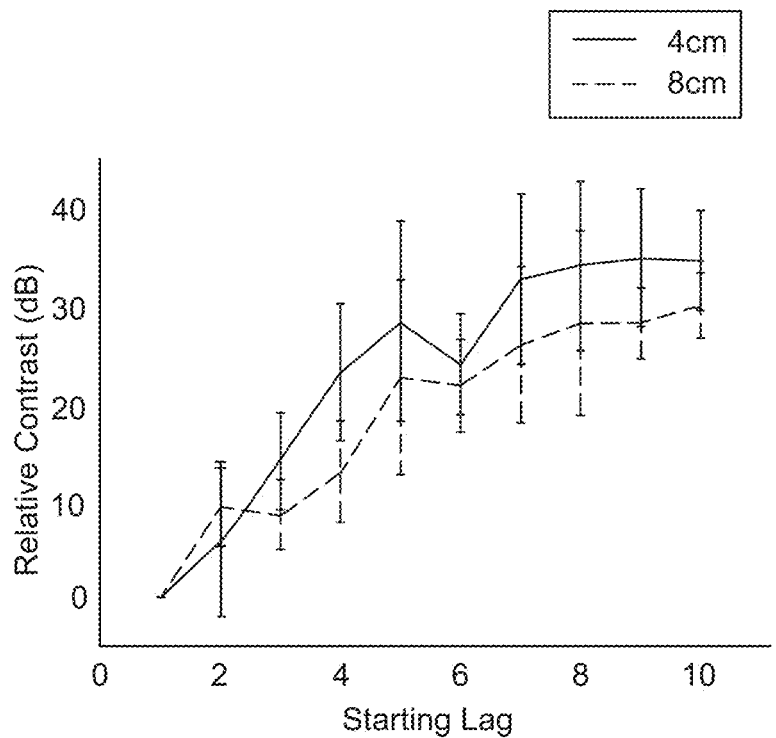
FIG. 13A shows variability of relative contrast for different imaging depths, according to an embodiment of the present disclosure.

FIG. 13A shows a graph of starting lag versus relative contrast for an MLSC measuring according to an embodiment of the present disclosure. FIG. 13A shows that for shallower depths, subsequent lags have a higher relative contrast.

Figure 13B:
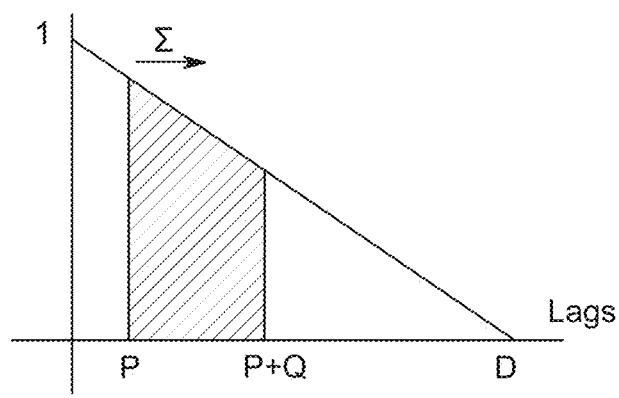
FIG. 13B shows which lags can be summed, according to an embodiment of the present disclosure.

FIG. 13B shows that, for an MLSC method, the middle lags are summed. The beginning and ending lags are omitted.

Figure 14A:
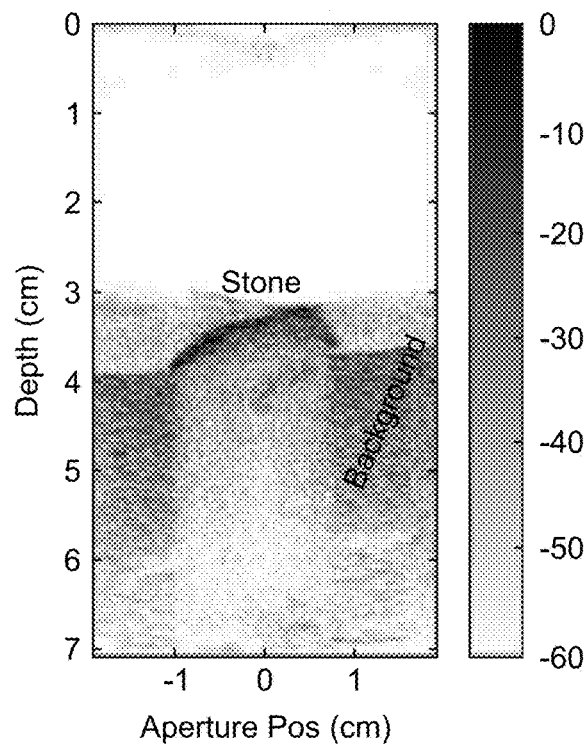
FIGS. 14A-B compare relative contrast for stone measurements, according to various embodiments of the present disclosure.
Figure 14B:
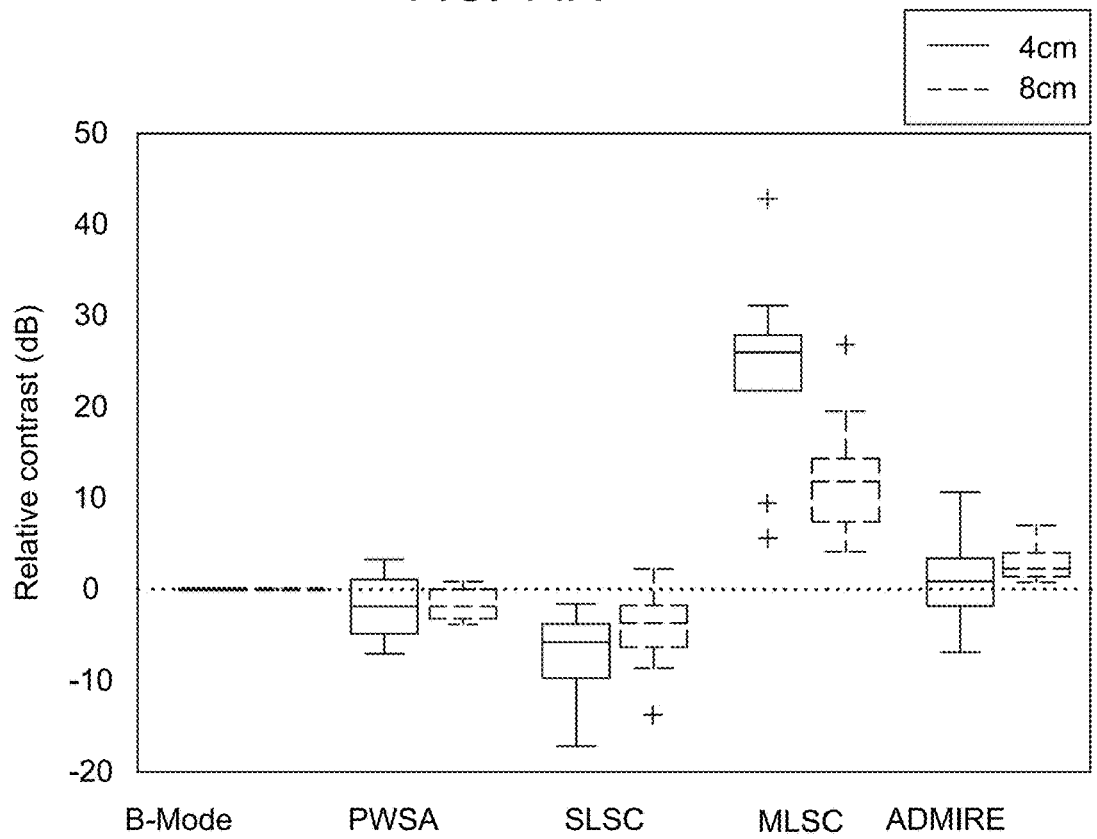

FIG. 14B compares relative contrast of the stone imaged in FIG. 14A. FIG. 14B compares between methods according to the present disclosure, including PWSA, SLSC, MLSC, and ADMIRE, against the conventional B-mode measuring. FIG. 14B shows that MLSC and ADMIRE in particular can provide greater contrast than the conventional B-mode method.

Figure 15A:
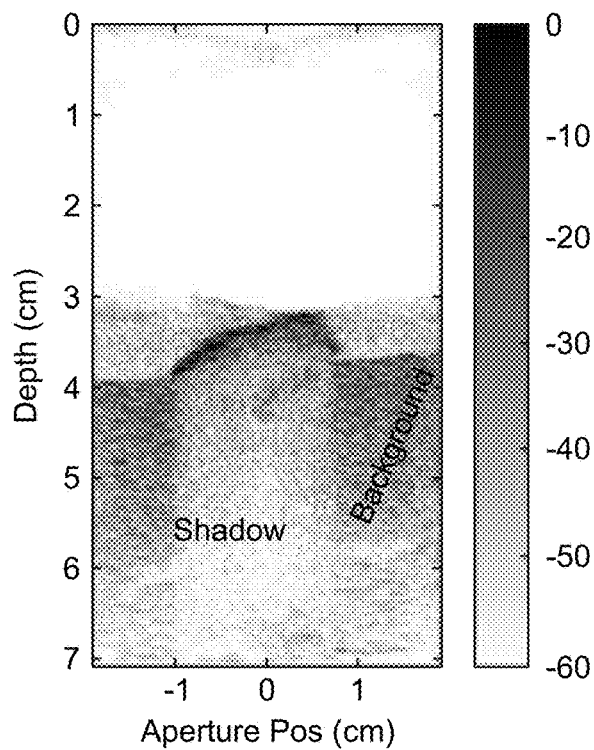
FIGS. 15A-B compare relative contrast for shadow sizing at different stone depths, according to various embodiments of the present disclosure.
Figure 15B:
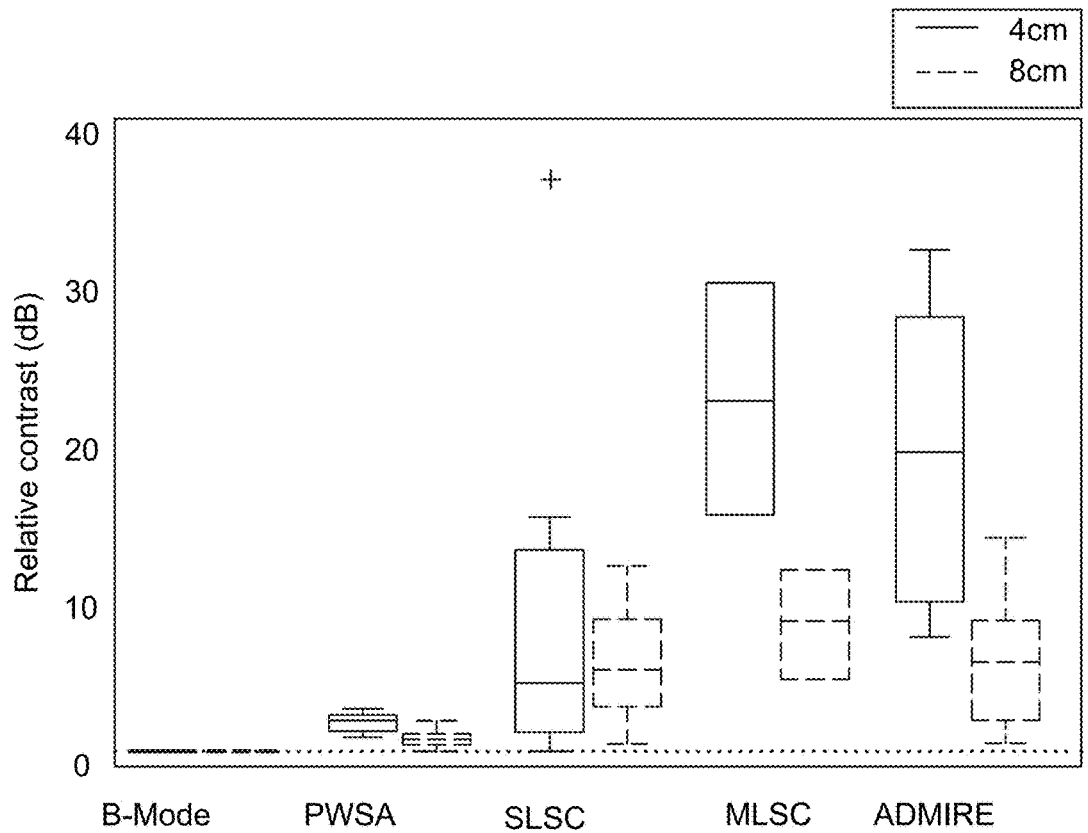

FIG. 15B compares relative contrast of the shadow imaged in FIG. 15A. FIG. 15B compares between methods according to the present disclosure, including PWSA, SLSC, MLSC, and ADMIRE, against the conventional B-mode measuring. FIG. 15B shows that all methods according to an embodiment of the present disclosure can provide greater contrast than the conventional B-mode method.

Figure 16A:
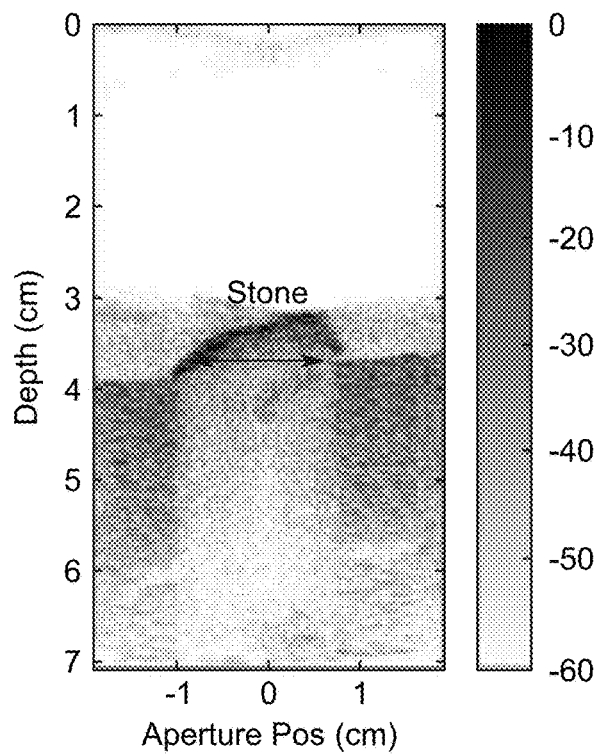
FIGS. 16A-B compare sizing errors in measured stone size, according to various embodiments of the present disclosure.
Figure 16B:
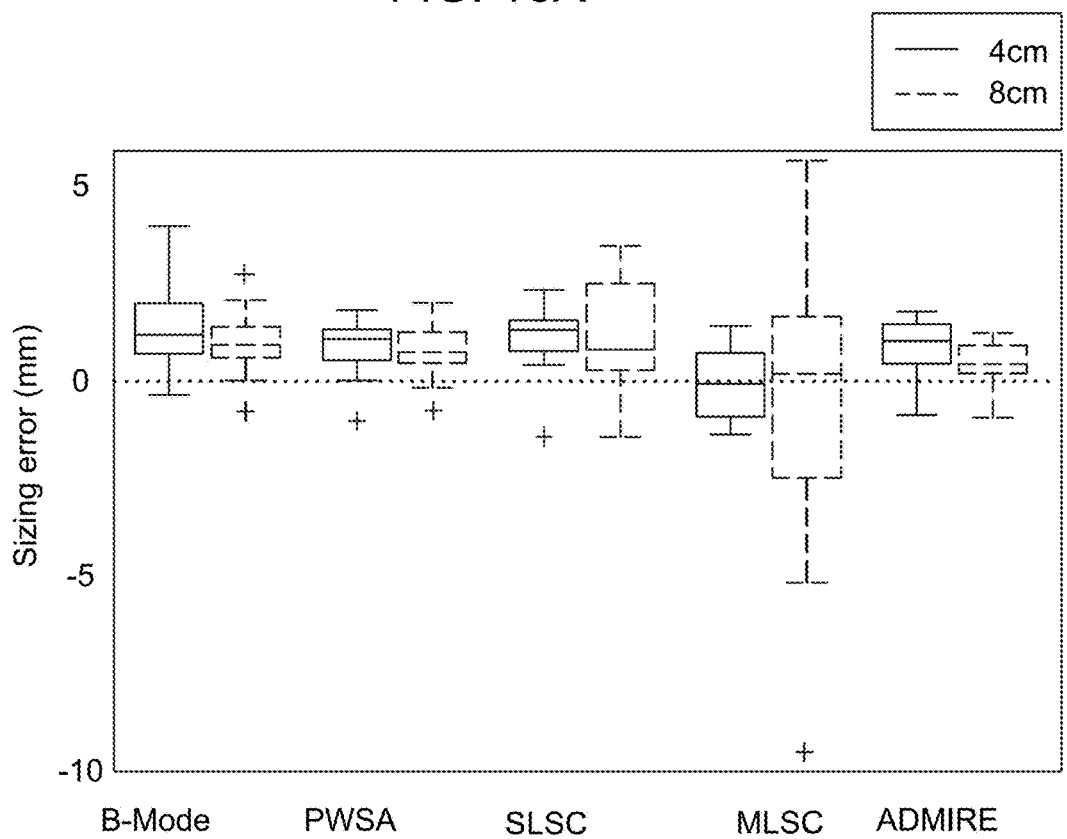

FIG. 16B compares sizing errors in measured stone size of the stone imaged in FIG. 16A. FIG. 16B compares between methods according to the present disclosure, including PWSA, SLSC, MLSC, and ADMIRE, against the conventional B-mode measuring. FIG. 16B shows that averaged sizing errors can be roughly similar across the various methods.

Figure 17A:
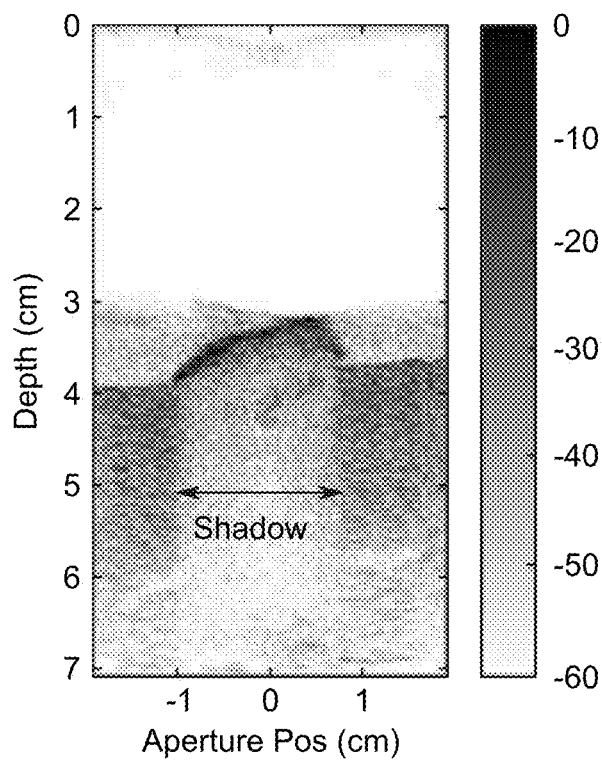
FIGS. 17A-B compare sizing errors in measured shadow size, according to various embodiments of the present disclosure.
Figure 17B:
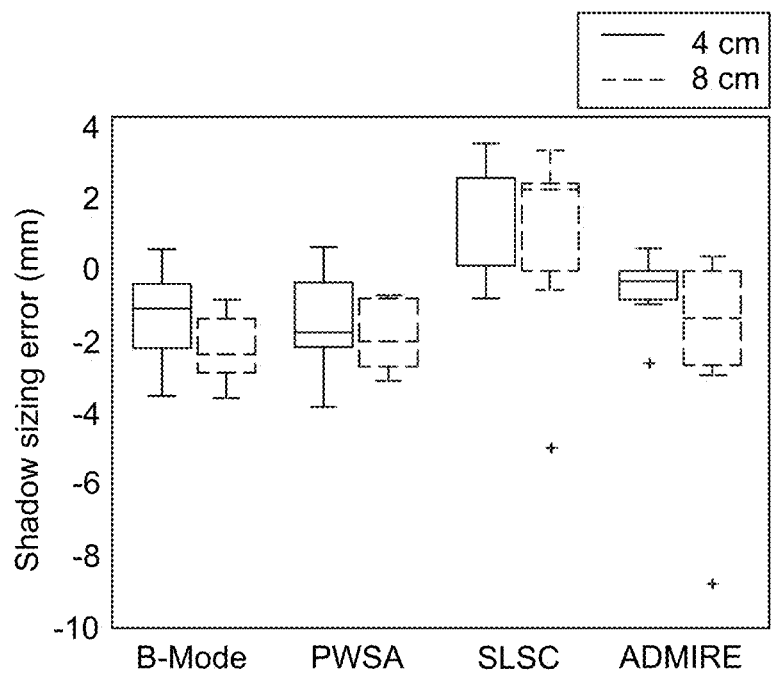

FIG. 17B compares sizing errors in measured shadow size of the stone imaged in FIG. 17A. FIG. 17B compares between methods according to the present disclosure, including B-Mode, PWSA, SLSC, and ADMIRE, against the conventional B-mode measuring. FIG. 17B shows that the ADMIRE method has greater accuracy than any other method for the 4 cm range.

Kidney Stone Imaging Methods for Obese Patients

It is widely acknowledged that obese patients are more difficult to image with ultrasound compared to their healthy weight counterparts. This increased difficulty in obese patients is attributable to increased skin-to-stone distance from thicker abdominal wall tissue. Abdominal wall tissue is a heterogeneous combination of subcutaneous fat, muscle, perirenal (or visceral) fat, and connective tissue, which can cause substantial variations in arrival time resulting in wavefront aberration and multiple reflections between soft tissue structures resulting in reverberation. These effects distort the ultrasound point spread function making all imaging tasks more difficult, including kidney stone detection and sizing.

As discussed previously, conventional B-mode ultrasound imaging is susceptible to degradation from a variety of mechanisms, including attenuation, diffraction-limitations, reverberation (or multiple scattering), gross sound-speed deviation, and sound speed and attenuation inhomogeneity (e.g. phase aberration). In addition, kidney stone imaging is uniquely challenged by the large impedance mismatch between the hard, elastic stone and the surrounding soft, visco-elastic tissue. The stone-tissue impedance mismatch is a factor of approximately 4-5, which is much larger than the typical mismatches encountered in soft tissues (less than a factor of 0.1). Specifically, the high impedance mismatch results in high levels of off-axis and internal stone reverberation clutter that inflate the apparent size of the stone, leading to inaccurate stone sizing. These challenges are all further complicated in obese patients by greater skin to stone distance and higher levels of wavefront aberration and reverberation.

Therefore, an embodiment of the present disclosure provides for integrating several additional steps into the disclosed ADMIRE and MLSC framework. First, the disclosed methods further provide for (1) harmonic sequencing to suppress reverberation, (2) aberration correction to suppress wavefront distortion, and (3) minimum variance beamforming to improve resolution and subsequent sizing. Therefore, ADMIRE provides a high-quality anatomical imaging and sizing tool, and MLSC provides a detection tool in obese patients.

In some embodiments, the disclosed method, as used for obese patients, provides for second harmonic imaging to reduce levels of wavefront aberration and reverberation Implementing MLSC with harmonic sequencing is challenging in obese patients because MLSC requires unfocused transmit beams; however, focused transmit beams are required to efficiently generate second harmonic signals within FDA acoustic exposure limits. To satisfy these conflicting design requirements, the present disclosure contemplates using MLSC sequences with low transmit f-numbers and shallow focal depths. In some examples of the present disclosure, shallow focal depths are less than approximately 4 cm deep to create the necessary unfocused harmonic beam at the stone depth of approximately 5 cm or more. This approach ensures efficient harmonic generation, and still creates an unfocused beam at the depth of the kidney allowing for the MLSC processing to work. Such a shallow focus approach allows imaging as deep as necessary, which is particularly necessary for obese patient measurements. The shallow focus allows generation of second harmonic energy and imaging using unfocused regions of a transmit beam.

In some embodiments of the present disclosure, the ADMIRE method is applied to individual transmit beams as a pre-processing step for MLSC. This restores MLSC contrast lost when imaging obese patients. Next, aberration profiles are computed using normalized cross-correlation based time-delay estimation across multiple channels and using a least squares reconstructed aberration profile to correct for the received wavefront's aberration. In some examples of the present disclosure, selection of the channel lags can be selected specifically for obese patients.

The above methods provide for accommodating the degradation from reverberation and aberration. However, the problem of increased skin-to-stone distance in obese patients also exacerbates the stone sizing problem. Sizing is driven by resolution, and resolution is directly proportional to imaging depth—resolution $\propto \lambda z/D$. Consequently, conventional ultrasound is particularly bad at sizing stones in obese patients. To address the limitations of conventional ultrasound, embodiments of the present disclosure provide for the integration of ADMIRE with minimum variance beamforming. Minimum variance beamforming produces images with improved resolution, particularly for bright, coherent objects such as stones. The advantage of combining ADMIRE with minimum variance beamforming is that minimum variance beamforming is impeded by the type of noise that the ADMIRE method resolves, so minimum variance can fail to realize improvements in some difficult to image patients without the assistance of ADMIRE. Therefore, a combination of ADMIRE and minimum variance beamforming provides better and more consistent stone sizing than with either method alone.

Figure 18:
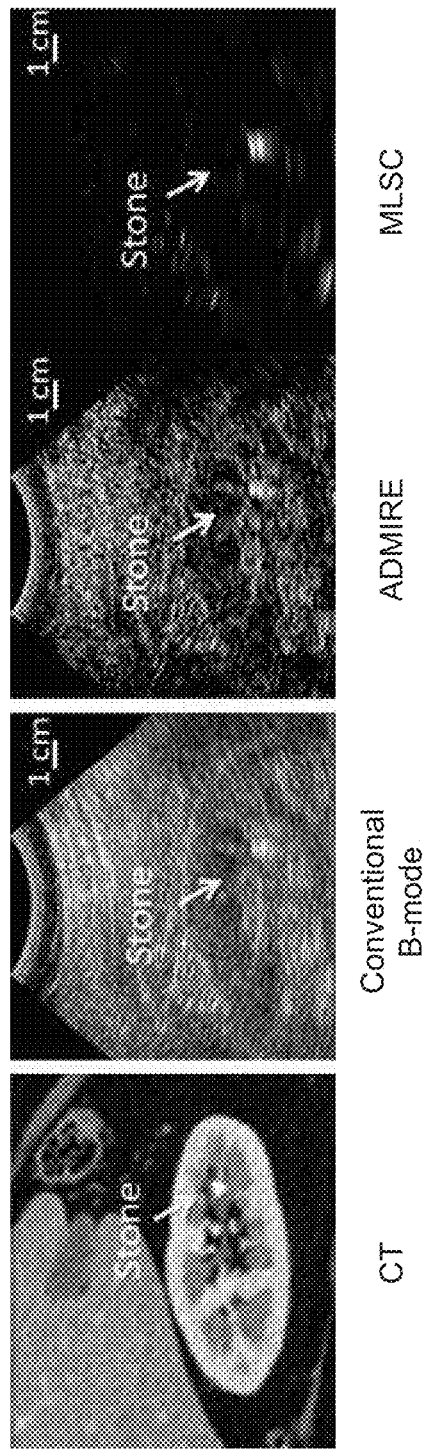
FIG. 18 compares kidney stone imaging between CT, conventional b-mode ultrasound, and the ADMIRE and MLSC methods of the present disclosure.

FIG. 18 compares kidney stone imaging between CT, conventional b-mode ultrasound, and the ADMIRE and MLSC methods of the present disclosure. Stone size on CT is 6.3 mm in width vs conventional B-mode (6.8 mm) and ADMIRE (6.2 mm) in the same orientation. Therefore, FIG. 18 demonstrates that anatomic detail and sizing are improved in ADMIRE as compared with the conventional B-mode ultrasound. MLSC further provides improved stone contrast compared to the conventional B-mode ultrasound; the contrast is 19 dB in the MLSC image versus 13 dB in the conventional B-mode ultrasound.

In order to study the role of obesity in stone imaging, it is necessary to accurately realize conventional sources of image degradation, namely reverberation and wavefront aberration. In some experimental techniques of representing abdominal wall tissue, the present disclosure provides for creating uniform sound speed within the abdominal wall tissue and preserving density variations; this eliminates aberration but maintains reverberation artifacts. The present disclosure further provides for manipulating the mechanical impedance to be constant throughout the abdominal tissue (i.e. manipulating speed and density simultaneously); thereby, reverberation can be eliminated while aberration induced artifacts are preserved. Aberration levels can be quantified by the receive aberration profile's root mean square and the full width half max (FWHM) of the profile's autocorrelation. In some examples, reverberation levels can be quantified as the power of the signal at the stone location when the stone is replaced by an anechoic cyst with no scattering.

Stone Roughness

It is necessary to have accurate measures and representations of the stone. Stone roughness remains uncharacterized in conventional methods for measuring and representing a stone. Simulating the roughness of stones is necessary as stone roughness can greatly impact visibility.

The present disclosure provides for quantifying stone roughness by imaging stones of varying compositions and then segmenting and reconstructing the stone surfaces. For example, roughness is quantified using $R_a$ and $R_{tm}$ parameters:

$$R_a = \frac{1}{n}\sum_{i=1}^{n} |y_i|$$

quantifies roughness as the mean absolute value of the stone's surface height $y_i$ over n number of sampling points, and $R_{tm}$ quantifies the mean of the maximum profile heights (i.e., peak heights minus valley heights) on the stone surface over a specified sampling distance computed as $$R_{tm} = \frac{1}{s}\sum_{i=1}^{s} \left(\max_i y_i - \min_i y_i\right).$$

s is the number of sampling lengths, and $$\max_i y_i - \min_i y_i$$

is the maximum height of the profile for the $i^{th}$ sampling length. The roughness, along with shape reconstructions, can be used to create simulated stone meshes for integration into a simulation tool, along with statistical roughnessparameter based domain/image construction methods. This allows simulation of stones with clinically relevant surface properties. In some examples of the present disclosure, the stones can be segmented and reconstructed using itk-SNAP, part of the National Library of Medicine's Insight Segmentation and Registration Toolkit (ITK).

Figure 19:
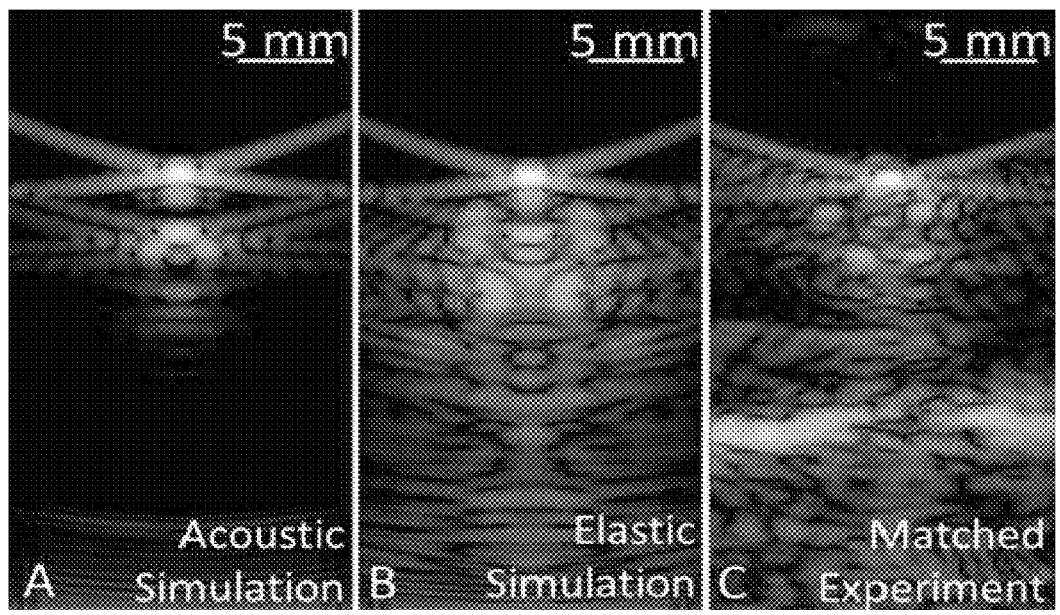
FIG. 19 compares simulations between an acoustic and an elastic stone, according to various embodiments of the present disclosure.

For example, FIG. 19 compares simulations, according to the method described above, with an acoustic (A) versus elastic (B) stone; the elastic stone (B) more appropriately matches the phantom experiment in (C). Parameters and imaging sequences are matched across cases and images are processed using the same algorithms. Thus, a simulation tool, according to the present disclosure, which models elastic wave propagation in the stone is essential for studying ultrasound image degradation in kidney stone specific scenarios. The dynamic range is the same in all images.

Figure 20:
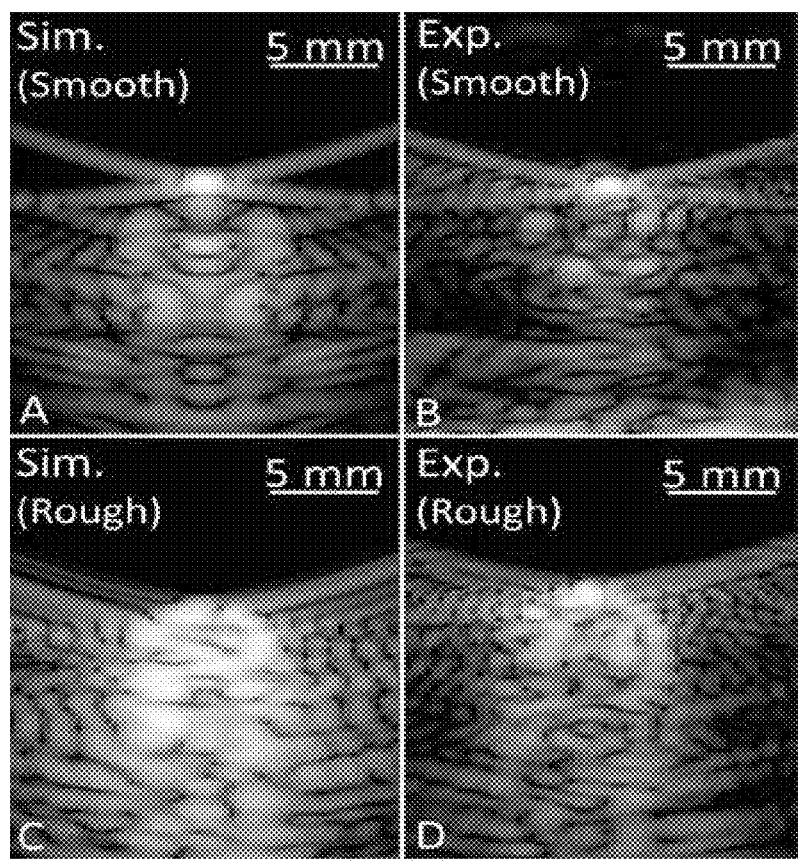
FIG. 20 shows simulation and experimental results of a stone-like object in a water bath, according to an embodiment of the present disclosure.

FIG. 20 shows simulation (A, C) and experimental (B, D) results of a stone-like object in a water bath. The smooth (A, B) and rough (C, D) surfaces have distinct appearances under simulation and experimental data. The image dynamic ranges match. Therefore, FIG. 20 shows the ability of a simulation according to the disclosed methods to accurately distinguish between rough and smooth stones.

FIG. 21A further shows ultrasound simulations with varying stone surface roughness from the smoothest (left) to the roughest (right) case. Roughness is quantified here as the peak deviation of the rough surface relative to the ultrasound wavelength, $\lambda$. The resulting change in B-mode image power (e.g. image brightness in this example) as a function of roughness is shown in FIG. 21B, which shows a linear trend up to a saturation point. This provides compelling evidence that roughness is a confounding factor for stone visualization. All images of FIGS. 21A-21B are made with the same dynamic range.

While various examples of the present invention have been described above, it should be understood that they have been presented by way of example only, and not limitation. Numerous changes to the disclosed examples can be made in accordance with the disclosure herein without departing from the spirit or scope of the invention. Thus, the breadth and scope of the present invention should not be limited by any of the above described examples. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular examples only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Other aspects of the invention are described in the attached documents with pages labeled "Supplemental Information Attorney Docket No. 077415-017141PL02". The contents of these documents are herein incorporated by reference in their entirety as if full set forth herein.

What is claimed is:

1. A method for detecting and sizing mineralized tissue comprising the steps of:
   imaging a region of interest containing the mineralized tissue with unfocused ultrasound beams and collecting imaging data;
   calculating a plurality of wavefront coherence values at and adjacent to the imaged region of interest based on the collected imaging data;
   generating pixels based on the plurality of wavefront coherence values;
   segmenting pixels of the imaged region of interest and pixels adjacent to the imaged region of interest based on their intensities;
   identifying a border of the mineralized tissue based on the segmenting; and
   determining a size of the mineralized tissue based on the border.

2. The method of claim 1, wherein the ultrasound beams are emitted using an array of transducer elements at a plurality of angles, wherein the array comprises (i) a reference element, (ii) a short lag region having a plurality of elements disposed closest to the reference element, (iii) a long lag region having a plurality of elements disposed farthest from the reference element and (iv) a mid-lag region having a plurality of elements disposed between the short lag and long lag regions.

3. The method of claim 2, wherein the step of calculating a plurality of wavefront coherence values further comprises summing wavefront coherence values corresponding to unfocused ultrasound beams emitted from the middle-lag region.

4. The method of claim 3, further comprising the steps of:
   windowing the unfocused ultrasound beams into a plurality of windows;
   multiplying each of the plurality of windows by the ultrasound beams;
   normalizing each of the plurality of windows by a signal energy of the unfocused ultrasound beams; and
   creating a measure of phase based on the normalizing of each of the plurality of windows.

5. The method of claim 1, wherein the step of imaging a region of interest further includes focusing the unfocused ultrasound beams using a transmit synthetic aperture.

6. The method of claim 1 further comprising identifying a shadow of the mineralized tissue based on the segmenting, wherein the size of the mineralized tissue is determined based on the border and shadow.

7. The method of claim 6, further comprising the steps of:
   modeling a plurality of sources of image degradation;
   receiving, at a transducer, the unfocused ultrasound beams;
   breaking the unfocused ultrasound beams into approximate points of origin; and
   reconstructing ultrasound pressure waves originating only from a particular location in the region of interest.

8. A system for detecting and sizing mineralized tissue, comprising:
- a processor; and
- a memory having stored thereon a computer program for causing the processor to carry out the following steps:
- imaging a region of interest containing the mineralized tissue with unfocused ultrasound beams and collecting imaging data;
- calculating a plurality of wavefront coherence values at and adjacent to imaged region of interest based on the collected imaging data;
- generating pixels based on the plurality of wavefront coherence values;
- segmenting pixels of the imaged region of interest and pixels adjacent to the imaged region of interest based on their intensities;
- identifying a border of the mineralized tissue based on the segmenting; and
- determining a size of the mineralized tissue based on the border.

9. The system of claim 8, wherein the ultrasound beams are emitted using an array of transducer elements at a plurality of angles, wherein the array comprises (i) a reference element, (ii) a short lag region having a plurality of elements disposed closest to the reference element, (iii) a long lag region having a plurality of elements disposed farthest from the reference element and (iv) a mid-lag region having a plurality of elements disposed between the short lag and long lag regions.

10. The system of claim 9, wherein the step of calculating a plurality of wavefront coherence values further comprises summing wavefront coherence values corresponding to unfocused ultrasound beams emitted from the middle-lag region.

11. The system of claim 10, further comprising the steps of:
- windowing the unfocused ultrasound beams into a plurality of windows;
- multiplying each of the plurality of windows by the ultrasound beams;
- normalizing each of the plurality of windows by a signal energy of the unfocused ultrasound beams; and
- creating a measure of phase based on the normalizing of each of the plurality of windows.

12. The system of claim 8, wherein the step of imaging a region of interest further includes focusing the unfocused ultrasound beams using a transmit synthetic aperture.

13. The system of claim 8 further comprising identifying a shadow of the mineralized tissue based on the segmenting, wherein the size of the mineralized tissue is determined based on the border and the shadow.

14. The system of claim 13, further comprising the steps of:
- modeling a plurality of sources of image degradation;
- receiving, at a transducer, the unfocused ultrasound beams;
- breaking the unfocused ultrasound beams into approximate points of origin; and
- reconstructing ultrasound pressure waves originating only from a particular location in the region of interest.

* * * * *